United States Patent [19]
Akagi et al.

[11] Patent Number: 5,698,544
[45] Date of Patent: Dec. 16, 1997

[54] CEPHEM COMPOUND, PROCESS FOR PRODUCING THE COMPOUND, AND ANTIMICROBIAL COMPOSITION CONTAINING THE SAME

[75] Inventors: Hiroshi Akagi; Masaru Yasui; Takae Yamada; Masahiro Ito; Akio Hyodo; Hideaki Hanaki, all of Tokushima, Japan

[73] Assignees: Otsuka Kagaku Kabushiki Kaisha, Osaka; Taiho Pharmaceutical Co., Ltd., Tokyo, both of Japan

[21] Appl. No.: 537,856

[22] PCT Filed: Mar. 17, 1995

[86] PCT No.: PCT/JP95/00471

§ 371 Date: Nov. 16, 1995

§ 102(e) Date: Nov. 16, 1995

[87] PCT Pub. No.: WO95/25109

PCT Pub. Date: Sep. 21, 1995

[30] Foreign Application Priority Data

Mar. 17, 1994 [JP] Japan ............................. 6-046737

[51] Int. Cl.[6] ...................... C07D 501/57; A61K 31/545
[52] U.S. Cl. .................. 514/203; 514/204; 540/224; 540/225
[58] Field of Search .................. 514/203, 204; 540/221, 222, 224, 225, 226

[56] References Cited

U.S. PATENT DOCUMENTS

| | | | |
|---|---|---|---|
| 4,584,290 | 4/1986 | Takaya et al. | 514/206 |
| 4,861,769 | 8/1989 | Takaya et al. | 514/202 |
| 5,403,835 | 4/1995 | Nakagawa et al. | 514/206 |
| 5,585,485 | 12/1996 | Ascher et al. | 540/225 |
| 5,593,985 | 1/1997 | Kim et al. | 514/203 |

FOREIGN PATENT DOCUMENTS

| | | |
|---|---|---|
| 0 111 281 A3 | 6/1984 | European Pat. Off. |
| 0 188 254 A2 | 7/1986 | European Pat. Off. |
| 0 630 899 A1 | 12/1994 | European Pat. Off. |

*Primary Examiner*—Mukund J. Shah
*Assistant Examiner*—Pavanaram K. Sripada
*Attorney, Agent, or Firm*—Armstrong, Westerman, Hattori, McLeland & Naughton

[57] ABSTRACT

The present invention provides a cephem compound having a high antimicrobial activity against various pathogenic bacteria.

The cephem compound of the invention is represented by the formula

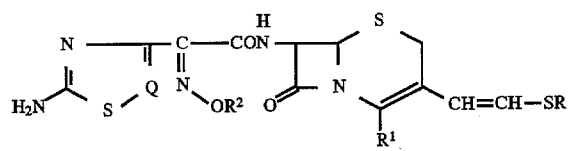

wherein Q represents CH or N, $R^1$ represents a carboxylate or the like, $R^2$ represents a hydrogen atom, and R represents

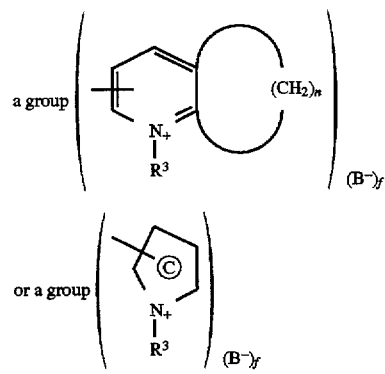

wherein $R^3$ represents a group $—(CH_2)_m—Y$ (wherein m is an integer of 1 to 5, and Y represents a quaternary ammonium group) or the like, n is an integer of 0 to 4, $B^-$ represents an anion, f is 0 or 1 when $R^1$ represents a carboxylate, and 2 when $R^1$ represents a carboxyl group, and the ring C represents a 5-membered heterocyclic group of not more than 4 nitrogen atoms, which may be substituted by a lower alkyl group.

8 Claims, No Drawings

CEPHEM COMPOUND, PROCESS FOR PRODUCING THE COMPOUND, AND ANTIMICROBIAL COMPOSITION CONTAINING THE SAME

This application is a 371 of PCT/JP 95/00471 F.D. Mar. 17, 1995.

TECHNICAL FIELD

This invention relates to a novel cephem compound, a process for producing the compound and an antimicrobial composition comprising the same.

PRIOR ART

With the spreading use of third-generation cephalosporins in recent years, infectious diseases associated with methicillin-resistant *Staphylococcus aureus* (MRSA) are presenting serious problems. These cephalosporins of the third generation have potent activity against gram-negative bacilli but because of their relatively low activity against gram-positive cocci, the strains of *S. aureus* which are resistant to β-lactam antibiotics have increased in number and the resultant refractory infections constitute a serious threat today. The only therapeutic drug available for MRSA infections today is vancomycin which is a polypeptide antibiotic but since it has side effects such as eczema and renal toxicity, vancomycin calls for caution in administration.

Numerous cephalosporin antibiotics having a quaternary ammonium salt have been known. These compounds have a high antimicrobial activity but a low solubility in water. Because of this defect, an attempt to develop a medicament from the compound has been abandoned. For example, Japanese Unexamined Patent Publication No.130292/1984 (EP-A-111281) describes compounds having a thiovinyl quaternary ammonium salt in the 3-position of the cephalosporin skeleton but does not refer to the introduction of a new quaternary ammonium substituent in the skeleton. Furthermore, there is no disclosure in the publication that the disclosed compound is active against MRSA.

Generally the antimicrobial activity of conventional cephalosporin compounds against gram-positive cocci inclusive of MRSA decreases with an increase of its water-solubility. Namely the antimicrobial activity of cephalosporin compounds is in inverse relation to its water-solubility. Thus it has been very difficult to develop a cephalosporin compound having both a high water-solubility and an excellent antimicrobial activity. Now there is a need for development of a cephem compound which is superior in the activity against MRSA and also in the water-solubility.

DISCLOSURE OF INVENTION

It is an object of this invention to provide a novel cephem compound having a high water-solubility and an excellent antimicrobial activity and, in particular, a novel cephem compound which is active and highly safe against gram-positive cocci inclusive of MRSA.

For the purpose of accomplishing the above-mentioned object, the inventors of this invention synthesized and investigated a variety of cephem compounds and discovered that when a new quaternary ammonium group is introduced as a substituent into a compound having a thiovinyl quaternary ammonium salt in the 3-position of the cephalosporin skeleton, the resulting cephem compound is imparted a high water-solubility and a high antimicrobial activity, particularly against gram-positive cocci inclusive of MRSA. This invention has been developed on the basis of the above discovery.

The cephem compound of this invention is a novel compound represented by the formula (1)

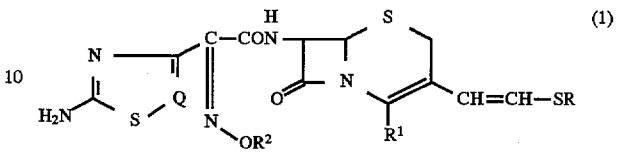

wherein Q represents CH or N, $R^1$ represents a carboxylate or a carboxyl group, $R^2$ represents a hydrogen atom, an optionally substituted lower alkyl group, an optionally substituted lower alkenyl group, an optionally substituted lower alkynyl group, an optionally substituted lower cycloalkyl group, an optionally substituted carboxy(lower)alkyl group, an optionally substituted hydroxy(lower)alkyl group, or an optionally substituted lower alkoxy(lower)alkyl group, and R represents

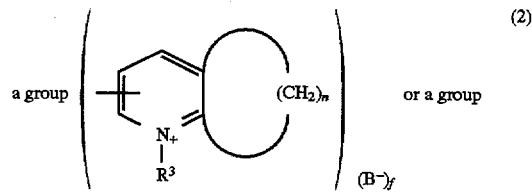

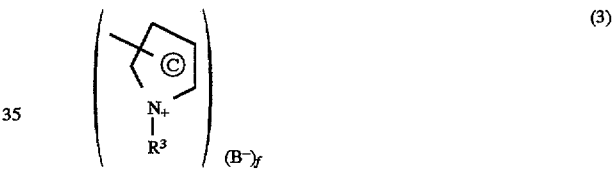

wherein $R^3$ represents a group $-(CH_2)_m-Y$ or a group $-(CH_2)_m-CO-Y$ (wherein m is an integer of 1 to 5, and Y represents a quaternary ammonium group), n is an integer of 0 to 4, $B^-$ represents an anion, f is 0 or 1 when $R^1$ represents a carboxylate, and 2 when $R^1$ represents a carboxyl group, and the ring C represents a 5-membered heterocyclic group of not more than 4 nitrogen atoms, which may be substituted by a lower alkyl group.

The respective groups mentioned in this specification more specifically include the following.

The lower alkyl group includes $C_{1-6}$ alkyl groups, such as methyl, ethyl, propyl, isopropyl, butyl, isobutyl, tert-butyl, pentyl and hexyl.

The lower alkenyl group includes $C_{2-6}$ alkenyl groups, such as vinyl, allyl, crotyl, 2-pentenyl and 2-hexenyl.

The lower alkynyl group includes $C_{2-6}$ alkynyl groups, such as ethynyl, 1-propynyl, 2-propynyl, 2-butynyl, 1-methyl-2-propynyl, 2-pentynyl and 2-hexynyl.

The lower cycloalkyl group includes cyclopropyl, cyclobutyl, cyclopentyl, and cyclohexyl.

The carboxy(lower)alkyl group includes carboxyalkyl groups having 1–6 carbon atoms in the alkyl moiety, such as carboxymethyl, 2-carboxyethyl, 3-carboxypropyl, 4-carboxybutyl, 5-carboxypentyl and 6-carboxyhexyl.

The hydroxy(lower)alkyl group includes hydroxy alkyl groups having 1–6 carbon atoms in the alkyl moiety, such as hydroxymethyl, 2-hydroxyethyl, 3-hydroxypropyl, 4-hydroxybutyl, 5-hydroxypentyl and 6-hydroxyhexyl.

The lower alkoxy(lower)alkyl group includes alkoxyalkyl groups having 1 to 4 carbon atoms in the alkyl moiety, such as methoxymethyl, methoxyethyl, methoxypropyl, methoxybutyl, ethoxymethyl, ethoxyethyl, ethoxypropyl and ethoxybutyl.

The ring represented by C is a 5-membered heterocyclic group comprising not more than 4 nitrogen atoms, which may be substituted by a lower alkyl group, thus including oxazole, thiazole, isoxazole, isothiazole, pyrazole, imidazole, thiadiazole, triazole, oxatriazole, thiatriazole, tetrazole, etc., which may respectively be substituted by one lower alkyl group on a ring nitrogen or carbon atom. Such heterocyclic rings can be specifically represented by the following structural formulas.

N = 1   V = O, S

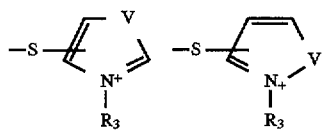

Oxazole    Isoxazole
Thiazole   Isothiazole

N = 2

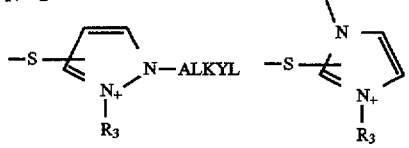

Pyrazole    Imidazole

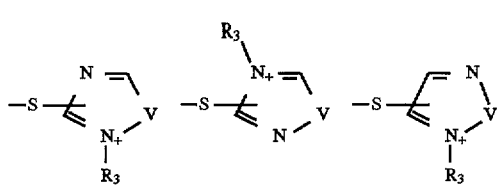

1,2,4-Oxadiazole      1,2,5-Oxadiazole
1,2,4-Thiadiazole     1,2,5-Thiadiazole

N = 3

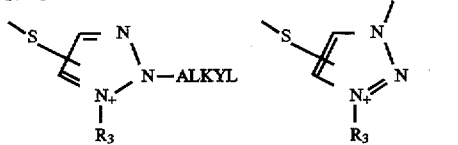

1,2,3-Triazole

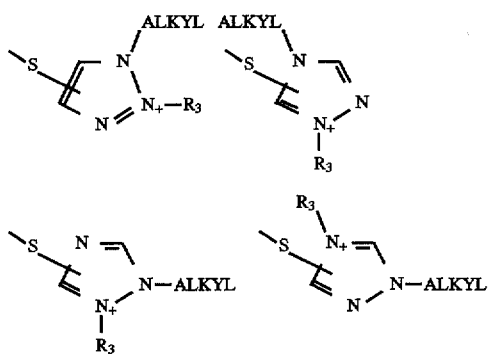

1,2,4-Trizole

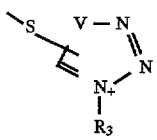

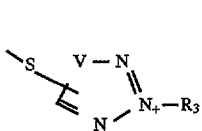 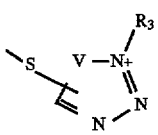

1,2,3,4-Oxatriazole
1,2,3,4-Thiatriazole

 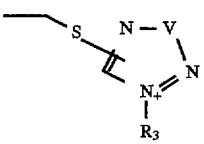

1,2,3,5-Oxatriazole
1,2,3,5-Thiatriazole

N = 4

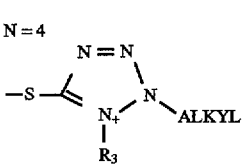 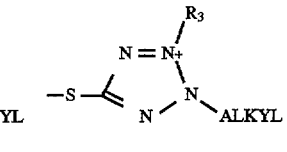

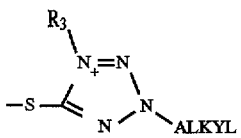 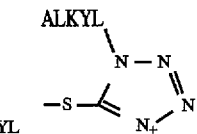

Tetrazole

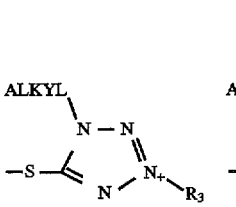 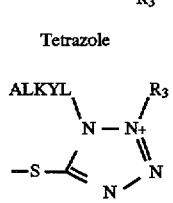

The quaternary ammonium group includes groups comprised of a 5-membered or 6-membered heterocyclic ring having 1 or 2 nitrogen atoms, and 1 or less oxygen and sulfur atom, such as groups represented by the formulas:

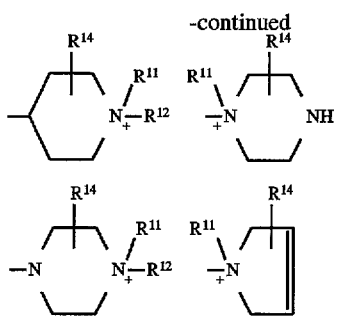

wherein $R^{11}$, $R^{12}$ and $R^{13}$ are the same or different and each represents a lower alkyl group, a lower alkenyl group, a hydroxy(lower)alkyl group, a carboxy(lower)alkyl group, a carbamoyl(lower)alkyl group, a lower alkanoyl(lower)alkyl group, a lower alkoxy(lower)alkyl group, a lower alkoxycarbonyl(lower)alkyl group, an amino(lower)alkyl group, a lower alkylamino(lower)alkyl group, a di(lower) alkylamino(lower)alkyl group or a sulfo(lower)alkyl group, and $R^{14}$ is a hydrogen atom, a halogen atom, an amino group, a lower alkyl group, a carboxy group, a hydroxy group, a lower alkoxy group, a lower alkoxy(lower)alkyl group, a hydroxy(lower)alkyl group, an amino(lower)alkyl group, a lower alkylamino(lower)alkyl group, a di(lower) alkylamino(lower)alkyl group, a di(lower)alkylamino group, a carboxy(lower)alkyl group, a carboxy(lower) alkylamino group, a carbamoyl group, a N-lower alkyl carbamoyl group, a formylamino group or an acylamino group.

The carbamoyl(lower)alkyl group includes carbamoylalkyl groups having 1–6 carbon atoms in the alkyl moiety, such as carbamoylmethyl, 2-carbamoylethyl, 3-carbamoylpropyl, 4-carbamoylbutyl, 5-carbamoylpentyl and 6-carbamoylhexyl.

The lower alkanoyl(lower)alkyl group includes alkanoylalkyl groups having 1–6 carbon atoms in the alkanoyl moiety and 1–6 carbon atoms in the alkyl moiety, such as formylmethyl, acetonyl, 3-acetylpropyl, 4-acetylbutyl, 6-propionylhexyl, 5-isobutyrylpentyl, hexanoylmethyl and 6-hexanoylhexyl.

The lower alkoxycarbony(lower)alkyl group includes alkoxycarbonylalkyl groups having 1–6 carbon atoms in the alkyl moiety, such as methoxycarbonylmethyl, methoxycarbonylethyl, methoxycarbonylpropyl, methoxycarbonylbutyl, ethoxycarbonylmethyl, ethoxycarbonylethyl, ethoxycarbonylpropyl and ethoxycarbonylbutyl.

The amino(lower)alkyl group includes aminoalkyl groups having 1–6 carbon atoms in the alkyl moiety, such as aminomethyl, 2-aminoethyl, 3-aminopropyl, 4-aminobutyl, 5-aminopentyl and 6-aminohexyl.

The lower alkylamino(lower)alkyl group includes alkylaminoalkyl groups having 1–5 carbon atoms in the alkylamino moiety and the alkyl moiety, such as methylaminomethyl, ethylaminomethyl, propylaminomethyl, butylaminomethyl, pentylaminomethyl, 2-methylaminoethyl, 3-methylaminopropyl, 4-methylaminobutyl and 5-methylaminopentyl.

The di(lower)alkylamino(lower)alkyl group includes dialkylaminoalkyl groups having 2–8 carbon atoms in the dialkylamino moiety and 1–6 carbon atoms in the alkyl moiety, such as dimethylaminomethyl, diethylaminomethyl, dipropylaminomethyl, dibutylaminomethyl, 2-dimethylaminoethyl, 3-dimethylaminopropyl, 4-dimethylaminobutyl, 5-dimethylaminopentyl and 6-dimethylaminohexyl.

The sulfo(lower)alkyl group includes sulfoalkyl groups having 1–5 carbon atoms in the alkyl moiety, such as methanesulfonic acid, ethanesulfonic acid, propanesulfonic acid, butanesulfonic acid and pentanesulfonic acid.

The halogen atom includes chlorine, bromine, fluorine and iodine.

The lower alkoxy group includes alkoxy groups having 1–6 carbon atoms, such as methoxy, ethoxy, propoxy, butoxy, pentyloxy and hexyloxy.

The di(lower)alkylamino group includes dialkylamino groups having 2–8 carbon atoms, such as dimethylamino, diethylamino, dipropylamino and dibutylamino.

The carboxy(lower)alkylamino group includes carboxyalkylamino groups having 1–6 carbon atoms in the alkyl moiety, such as carboxymethylamino, 2-carboxyethylamino, 3-carboxypropylamino, 4-carboxybutylamino, 5-carboxypentylamino and 6-carboxyhexylamino.

The acylamino group includes acylamino groups having 1–6 carbon atoms in the alkyl moiety, such as acetylamino, propionylamino, butyrylamino, isobutyrylamino, valerylamino and pivaloylamino.

The N-lower alkylcarbamoyl group includes N-alkylcarbamoyl groups having 1–4 carbon atoms in the alkyl moiety, such as methylcarbamoyl, ethylcarbamoyl, propylcarbamoyl and butylcarbamoyl.

The anion represented by $B^-$ includes the acid residues of inorganic acids such as hydrochloric acid, hydrobromic acid, nitric acid, sulfuric acid, perchloric acid, etc. and of organic acids such as methanesulfonic acid, ethanesulfonic acid, 2-chloroethanesulfonic acid, benzenesulfonic acid, p-toluenesulfonic acid, p-ethylbenzenesulfonic acid, p-chlorobenzenesulfonic acid, naphthalenesulfonic acid, trifluoroacetic acid, trifluoromethanesulfonic acid, formic acid, etc.

The cephemcarboxy-protecting group includes those protective ester residues which are conventionally used in the synthesis of cephem compounds as well as pharmacologically acceptable protective ester residues. The protective ester residues conventionally used in cephem synthesis are those ester residues which are stable in various chemical modifications of β-lactam compounds but can be easily cleaved off in the conversion to the pharmacologically acceptable protective ester residues which are described below. The pharmacologically acceptable protective ester residues are nontoxic ester residues which can be readily hydrolyzed in vivo and, as such, can be rapidly decomposed in the human blood and tissues. Such esters may be those known esters which are commonly used in the field of antibiotics, thus including the ester residues described in Japanese Unexamined Patent Publication No. 81380/1974 and H. E. Flynn (ed.): Cephalosporins and Penicillins, Chemistry and Biology (1972, Academic Press). As the preferred species may be mentioned $C_{1-18}$ alkyl groups such as methyl, ethyl, propyl, butyl, tert-butyl, 1,1-dimethylpropyl, 1-cyclopropylmethyl, pentyl, hexyl, decyl, undecyl, dodecyl, tetradecyl, hexadecyl, octadecyl, etc.; halo(lower)alkyl groups substituted by 1–3 chlorine, bromine or iodine atoms, such as iododecyl, chloromethyl, 2,2-dibromoethyl, 2,2,2-trichloroethyl, 2,2,2-tribromoethyl, etc.; methyl substituted by 1–3 phenyl groups which may be substituted by nitro or alkoxy, such as benzyl, diphenylmethyl, trityl, p-nitrobenzyl, o-methoxybenzyl, p-methoxybenzyl, di(p-methoxyphenyl)methyl, etc.; lower alkoxymethyl groups such as methoxymethyl, ethoxymethyl, n-propyloxymethyl, isopropyloxymethyl, n-butoxymethyl, isobutoxymethyl, etc.; lower alkylcarbonyloxy(lower)alkyl groups such as acetoxymethyl, acetoxyethyl, propionyloxyethyl, n-butyryloxymethyl, isobutyryloxymethoyl, pivaloyloxymethyl, 1-acetoxyethyl, pivaloyloxyethyl, pivaloyloxypropyl, 1-propionyloxybutyl, etc.; $C_{5-7}$ cycloalkylcarbonyloxy-lower alkyl groups such as cyclopentylcarbonyloxymethyl, cyclohexylcarbonyloxymethyl, etc.; benzylcarbonyloxy (lower)alkyl groups such as benzylcarbonyloxymethyl etc.; benzoyloxy(lower)alkyl groups such as benzoyloxymethyl, benzoyloxyethyl, etc.; lower alkoxycarbonyloxy(lower) alkyl groups such as methoxycarbonyloxymethyl, 1-ethoxycarbonyloxyethyl, 3-methoxy-carbonyloxypropyl, etc.; benzyloxy(lower)alkyl groups such as benzyloxymethyl, benzyloxyethyl, etc.; and such other groups as 2-cyano-1,1-dimethylethyl, bromobenzoylmethyl, p-nitrobenzoylmethyl, dimethylaminomethyl, methylthiomethyl, phenylthiomethyl, succinimidomethyl, 1,1-dimethyl-2-propenyl, 1,3-dimethyl-3-butenyl, 3-phthalidyl, crotonolacton-4-yl, γ-butyrolacton-4-yl, tetrahydropyranyl, dimethylaminoethyl, dimethylchlorosilyl, trichlorosilyl, (2-oxo-1,3-dioxoden-4-yl)methyl, (5-methyl-2-oxo-1,3-dioxoden-4-yl)methyl, (5-phenyl-2-oxo-1,3-dioxoden-4-yl)methyl, pyridine-1-oxide-2-methyl and quinoline-1-oxide-2-methyl.

The nontoxic salt of the compound of the formula (1) includes medicinally acceptable salts such as hydrochloride, hydrobromide, hydroiodide, sulfate, etc., salts with organic carboxylic acids., such as citrate, maleate, lactate, tartrate, etc., salts with organic sulfonic acids such as methane sulfonate, hydroxymethane sulfonate, aminoethane sulfonate, benzene sulfonate, toluene sulfonate, etc., salts with amino acids, such as arginine salt, lysine salt, serine salt, aspartate, glutamate, aminoacetate, etc., alkali metal salts such as sodium salt, potassium salt, lithium salt, etc. and alkaline earth metal salts such as calcium salt, magnesium salt, etc.

The group represented by Q is preferably CH. The group represented by $R^1$ is preferably a carboxylate. The group represented by $R^2$ is preferably a hydrogen atom or a lower cycloalkyl group, more preferably a hydrogen atom. The group represented by R is preferably a group represented by the formula

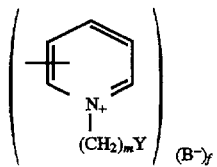

wherein m is preferably 2 or 3, Y is a lower alkyl group, a hydroxy(lower)alkyl group, a carboxy(lower)alkyl group, a carbamoyl(lower)alkyl group, a lower alkanoyl(lower)alkyl group, a lower alkoxycarbonyl(lower)alkyl group, or a quaternary ammonium salt group substituted by a sulfo(lower) alkyl group, a morpholinio group substituted by a lower alkyl group, or a piperidinio group substituted by a lower alkyl group, and B is preferably a halogen atom, more preferably a chlorine atom.

The preferred species of the compound of the formula (1) and the nontoxic salt thereof are as follows:

chloride 7-[2-hydroxyimino-2-(2-aminothiazol-4-yl) acetamido]-3-[2-(1-(3-(4-methylmorpholinio)propyl)-4-pyridinio)thiovinyl]-3-cephem-4-carboxylate or its salt, chloride 7-[2-hydroxyimino-2-(2-aminothiazol-4-yl) acetamido]-3-[2-(1-(2-trimethylammonioethyl)-4-pyridinio)thiovinyl]-3-cephem-4-carboxylate or its salt, chloride 7-[2-hydroxyimino-2-(2-aminothiazol-4-yl) acetamido]-3-[2-(1-(2-carbamoylmethyl-dimethylammonioethyl)-4-pyridinio)thiovinyl]-3-cephem-4-carboxylate or its salt, chloride 7-[2-hydroxyimino-2-(2-aminothiazol-4-yl) acetamido]-3-[2-(1-(2-(4-methylmorpholinio)ethyl)-4-pyridinio)thiovinyl]-3-cephem-4-carboxylate or its salt, chloride 7-[2-hydroxyimino-2-(2-aminothiazol-4-yl) acetamido]-3-[2-(1-(2-acetonyl-dimethylammonioethyl)-4-pyridinio)thiovinyl]-3-cephem-4-carboxylate or its salt, chloride 7-[2-hydroxyimino-2-(2-aminothiazol-4-yl) acetamido]-3-[2-(1-(2-(1-methylpiperidinio)ethyl)-4-pyridinio)thiovinyl]-3-cephem-4-carboxylate or its salt, 7-[2-hydroxyimino-2-(2-aminothiazol-4-yl)acetamido]-3-[2-(1-(2-carboxylate methyl- dimethylammonioethyl)-4-pyridinio)thiovinyl]-3-cephem-4-carboxylate or its salt, chloride 7-[2-hydroxyimino-2-(2-aminothiazol-4-yl) acetamido]-3-[2-[1-(2-hydroxyethyl-dimethylammonioethyl)-4-pyridinio)thiovinyl]-3-cephem-4carboxylate or its salt, chloride 7-[2-hydroxyimino-2-(2-aminothiazol-4-yl) acetamido]-3-[2-(1-(2-ethyloxycarbonylmethyldimethylammonioethyl)-4-pyridinio])thiovinyl]-3-cephem-4-carboxylate or its salt, chloride 7-[2-cyclopentyloxyimino-2-(2-aminothiazol-4-yl) acetamide]-3-[2-(1-(2-trimethylammonioethyl)-4-pyridinio)thiovinyl]-3-cephem-4-carboxylate or its salt, and 7-[2-hydroxyimino-2-(2-aminothiazol-4-yl)acetamido]-3-[2-(1-(sulfonate ethyl-dimethylammonioethyl)-4-pyridinio)thiovinyl]-3-cephem-4-carboxylate or its salt.

The compound (1) of this invention and its starting compounds include cis- and trans-isomers and mixtures of such cis- and trans-isomers.

In the case of compound (1), the cis-isomer, for instance, means one of the geometrical isomers having the partial structure of the following formula (4) and the trans-isomer means the other geometrical isomer having the partial structure of the following formula (5).

While the compound (1) and a salt thereof can be produced by various processes, the process I described below is preferred.

Process-I

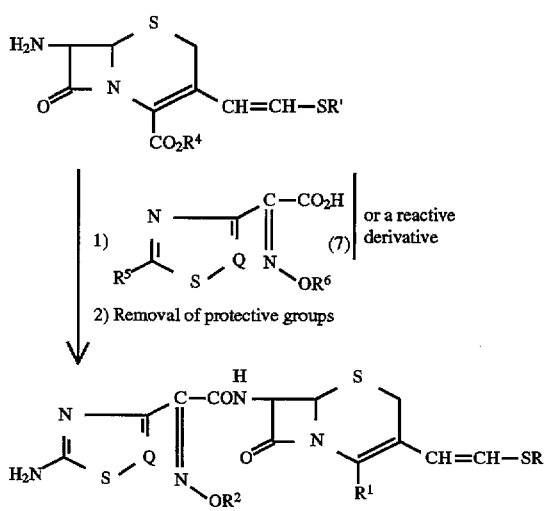

wherein $R^4$ represents a cephemcarboxy-protective group; R' represents

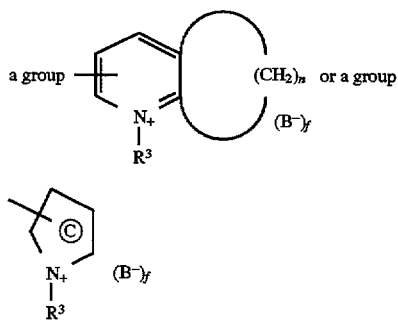

wherein $R^3$, n, $B^-$ and C are as defined hereinbefore; $R^5$ represents an amino group or a protected amino group; $R^6$ represents an oxime-protective group or a group represented by $R^{2'}$ (a group $R^2$ other than a hydrogen atom); and Q, R, $R^1$ and $R^2$ are as defined hereinbefore.

According to the above process I, a compound of the formula (1) can be produced by subjecting an amine compound of the formula (6) and a carboxylic acid compound of the formula (7) or a reactive derivative thereof, as derived by activating its carboxyl group, to the conventional amide bond-forming reaction and optionally removing the protective groups from the resultant product.

The carboxy-protective group designated by $R^4$ herein includes those carboxy-protective groups which are conventionally used in this field and can be easily removed, e.g. tri(lower)alkylsilyl groups such as trimethylsilyl etc., benzhydryl, p-methoxybenzyl, tertbutyl, p-nitrobenzyl and phenacyl.

The protective group of the protected amino group $R^5$ includes a broad range of protective groups which can be easily eliminated under mild conditions, e.g. tri(lower) alkylsilyl groups such as trimethylsilyl etc., acyl-type protective groups such as formyl, trifluoroacetyl, acetyl, tert-butylcarbonyl, methoxyacetyl, benzyloxycarbonyl, p-nitrobenzyloxycarbonyl, etc., and aralkyl-type protective groups such as benzyl, benzhydryl, trityl and so on.

The oxime-protective group $R^6$ includes those protective groups which can be easily eliminated under mild conditions and are conventionally employed in this field, such as acetyl, trityl, tetrahydropyranyl and so on.

The reaction between compound (6) and compound (7) or a reactive derivative of the latter can be carried out under conditions similar to those of known amide bond-forming reactions.

The reactive derivative of compound (7) includes acid halides such as acid chloride, acid bromide, etc., acid anhydrides with various acids such as substituted phosphoric acids, dialkyl phosphites, sulfurous acid, thiosulfuric acid, alkyl carbonate, organic carboxylic acids, etc., symmetric acid anhydrides, active acid amides with imidazole, dimethylpyrazole, etc., and active esters such as p-nitrophenyl ester, phenylthioester, carboxymethylthioester, etc. or esters with N-hydroxy compounds such as N-hydroxypiperidine, N-hydroxysuccinimide, N-hydroxyphthalimide and so on.

When this invention is practiced using compound (7) in the form of a free carboxylic acid, it is preferable to use a condensing agent such as N,N-diethylcarbodiimide, N,N-dicyclohexylcarbodiimide or the like.

The solvent that can be used in the above reaction may be virtually any solvent that does not take part in the reaction and the reaction is generally carried out with cooling or in the neighborhood of room temperature. The solvent mentioned above includes ethers such as diethyl ether, tetrahydrofuran, dioxane, etc., halogenated hydrocarbons such as dichloromethane, dichloroethane, chloroform, carbon tetrachloride, etc., aromatic hydrocarbons such as benzene, toluene, etc., amines such as pyridine, piperidine, triethylamine, etc., esters such as ethyl acetate, ethyl formate, etc., aprotic polar solvents such as dimethylformamide, hexamethylphosphoric triamide, dimethyl sulfoxide, etc., and acetone, and mixtures of such solvents.

Depending on the reactive derivative of the carboxylic acid to be used, the reaction may be preferably conducted in the presence of a basic compound. The basic compound includes organic bases, e.g. trialkylamines such as triethylamine, tributylamine, etc., pyridine, picoline, 1,8-diazabicyclo[5.4.0]-7-undecene, etc. and inorganic bases, e.g. sodium hydrogen carbonate, potassium hydrogen carbonate, sodium carbonate, potassium carbonate, sodium hydroxide, potassium hydroxide and so on.

The amount of the carboxylic acid compound of the formula (7) or a reactive derivative thereof relative to the amine compound of the formula (6) for use in this reaction is generally about 1 to about 10 mol equivalents, preferably about 1 to about 3 mol equivalents. The amount of said basic compound relative to the amine compound of the formula (6) is generally about 1 to about 30 mol equivalents, preferably about 2 to about 10 mol equivalents. The reaction time is generally about 1 to about 24 hours, preferably about 1 to about 6 hours.

Removal of protective groups from the amide bonding product thus obtained can be carried out as follows. For example, when the protective group is a tri(lower)alkylsilyl group, it can be removed with water. When the protective group is benzhydryl, trityl, p-methoxybenzyl, tert-butyl or formyl, for instance, it can be removed with formic acid, hydrochloric acid, trifluoroacetic acid, anisole-trifluoroacetic acid, acetic acid, phenol, cresol or the like. After completion of the reaction, the compound of the formula (1) according to this invention can be produced by purification through column chromatography using a hyperporous polymer such as Diaion HP-20, HP-21, SP-207 or CHP-20P (Mitsubishi Kasei Corporation), Amberlite XAD-2 (Rhom & Haas Co.) or the like.

Process-II

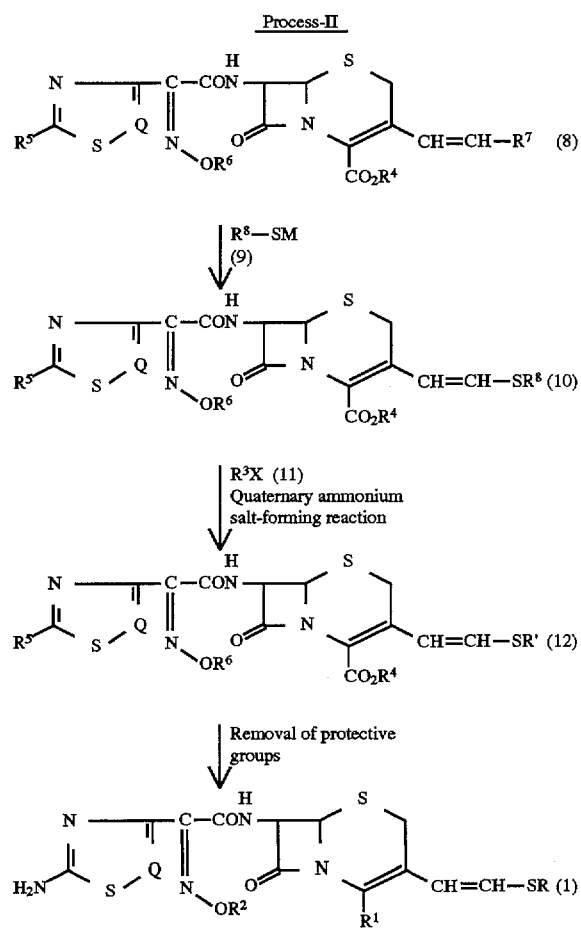

wherein Q, R, $R^1$, $R^2$, $R^3$, $R^4$, $R^5$, $R^6$ and R' are as defined hereinbefore; $R^7$ represents a halogen atom, a lower acyloxy group or a sulfonyloxy group; $R^8$ represents

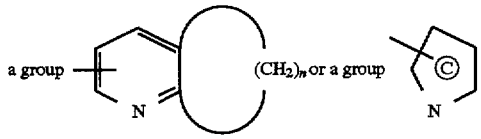

wherein C and n are as defined hereinbefore; X represents a halogen atom; and M represents a hydrogen atom or a metal atom.

Referring to the above production process II, the compound of the formula (1) according to this invention can be obtained by reacting a cephalosporin compound of the formula (8) or a salt thereof with a mercapto compound of the formula (9), then reacting the resultant compound of the formula (10) with a halogenated organic compound of the formula (11) and removing the protective groups from the resultant compound of the formula (12).

The reaction between compound (8) and compound (9) is generally carried out in an organic solvent or a mixture of a hydrophilic organic solvent with water. Examples of useful organic solvents are ketones including acetone etc., halogenated hydrocarbons such as chloroform, dichloromethane, dichloroethane, etc., ethers such as diethyl ether, tetrahydrofuran, dioxane, etc., acetonitrile, alcohols such as methanol, ethanol, etc., dimethyl sulfoxide, dimethylformamide, water, phosphate buffers, etc. To hasten the reaction, a base or a salt may be added to the reaction system. As examples of said base or salt may be reckoned inorganic bases such as sodium hydroxide, potassium hydroxide, sodium carbonate, potassium carbonate, etc. and organic amines, e.g. trialkylamines such as triethylamine, diisopropylamine, etc. As said salt, quaternary ammonium salts such as tetrabutylammonium salt can be mentioned by way of example. The proportions of compounds 8 and 9 are not critical, but compound 9 is generally used in an amount of 1 to 5 equivalents, preferably 1 to 2 equivalents, based on compound 8. This reaction is generally carried out with cooling or around room temperature.

The solvent which can be used for the reaction between compound (10) and compound (11) includes halogenated hydrocarbons such as dichloromethane, dichloroethane, chloroform, carbon tetrachloride, etc., aromatic hydrocarbons such as benzene, toluene, xylene, etc., ethers such as diethyl ether, tetrahydrofuran, dioxane, etc., and acetonitrile. The proportions of compounds (10) and (11) are dependent on the species of compound (11) and can not be specifically limited, but usually the amount of compound (11) is 1 to 100 equivalents, preferably 5 to 50 equivalents, based on compound (10). This reaction is conducted at a temperature ranging from room temperature to about 80° C., preferably at about 20° to about 50° C., and generally goes to completion in about 1 to about 20 hours.

Examples of the halogenated organic compound of the formula (11) are 2-bromo-ethyltrimethylammonium iodide, 3-bromo-propyltrimethylammonium iodide, 2-bromoethyl-hydroxyethyl-dimethylammonium iodide, 2-bromoethyl-carbamoylmethyl-dimethylammonium iodide, N-(2-bromoethyl)-N-methyl-morphonium iodide, N-(2-bromoethyl)-N-carbamoylmethyl-morphonium iodide, N-(2-bromoethyl)-N-methyl-piperidinium iodide, 1-(2-bromoethyl)-1-methyl-piperazinium iodide, 1-(2-bromoethyl)-1-carbamoylmethyl-piperazinium iodide, 1-(2-bromoethyl)-1,4-dimethyl-piperazinium iodide, 1-(2-bromoethyl)-1-carbamoylmethyl-4-methyl-piperazinium iodide, 1-(2-bromoethyl)-4,4-dimethyl-piperazinium iodide, 1-(2-bromoethyl)-1-methyl-pyrrolidinium iodide, 1-(2-bromoethyl)-1-carbamoylmethyl-pyrrolidinium iodide, etc.

From the compound of the formula (12) thus obtained, the protective groups can be eliminated by the procedures described for Process I, whereby the compound of the formula (1) according to this invention is easily obtained.

Process-III

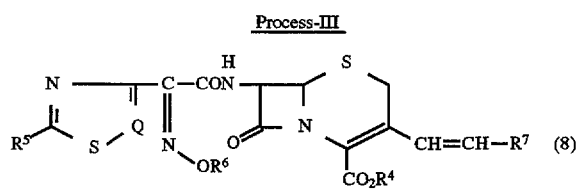

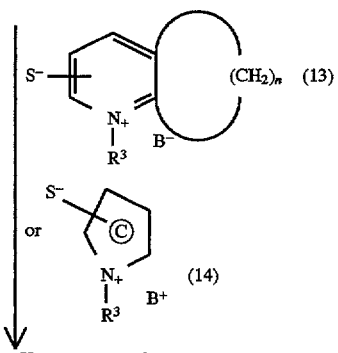

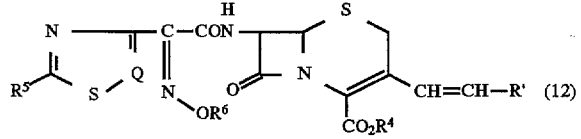

wherein Q, R³, R⁴, R⁵, R⁶, R⁷, R', B⁻ and C are as defined hereinbefore.

The compound of the formula (12) can also be prepared by the above process-III. According to the process-III, the compound of the formula (12) can be prepared by reacting the compound of the formula (8) with the guaternized mercapto compound of the formula (13) or (14).

The reaction between the compound of the formula (8) and the compound of the formula (13) or (14) can be conducted under the same conditions as in the above reaction of the compound of the formula (8) with the compound of the formula (9).

Process-III

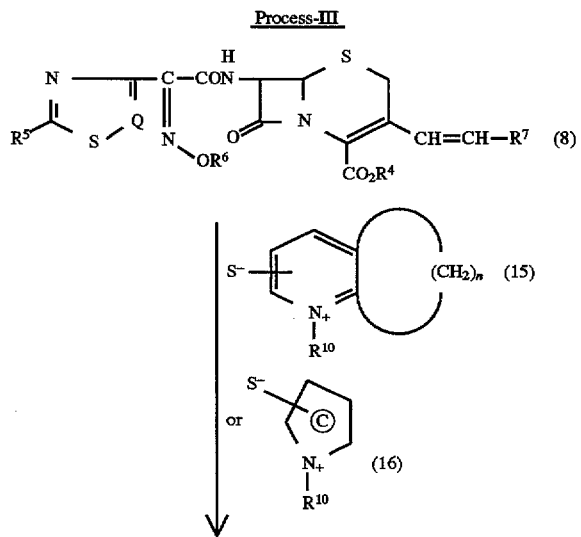

-continued
Process-III

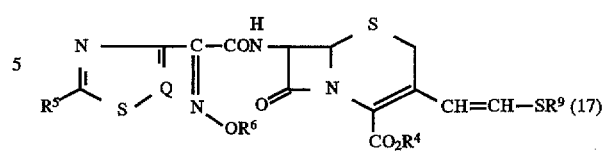

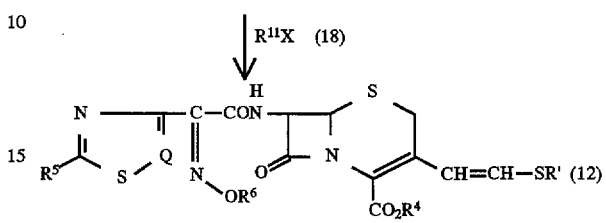

wherein Q, R⁴, R⁵, R⁶, R⁷ and R' are as defined hereinbefore, R⁹ is represented by the formula

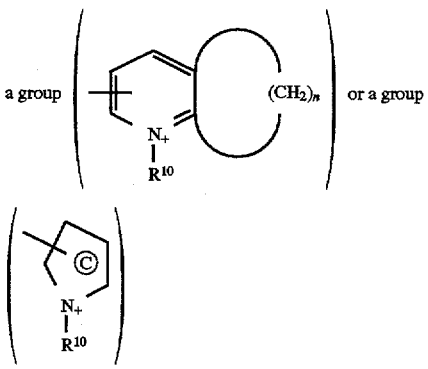

wherein $R^{10}$ represents a group $-(CH_2)_m-Z$ or a group $-(CH_2)_m-CO-Z$ (wherein m is an integer of 1 to 5, and Z represents a tertiary amino group), $R^{11}$ represents a lower alkyl group, a lower alkenyl group, a hydroxy(lower)alkyl group, a carboxy(lower)alkyl group, a carbamoyl(lower) alkyl group, a lower alkanoyl(lower)alkyl group, a lower alkoxy(lower)alkyl group, a lower alkoxycarbonyl(lower) alkyl group, an amino(lower)alkyl group, a lower alkylamino(lower)alkyl group, a di(lower)alkylamino (lower)alkyl group or a sulfo(lower)alkyl group, and n is an integer of 0 to 4.

The compound of the formula (12) can also be prepared by the above process-IV.

The reaction between the compound of the formula (8) and the compound of the formula (15) or (16) can be conducted under the same conditions as in the above reaction of the compound of the formula (8) with the compound of the formula (9). The reaction between the compound of the formula (17) and the compound of the formula (18) can be conducted under the same conditions as in the above reaction of the compound of the formula (10) with the compound of the formula (11). The halogenated organic compound of the formula (18) includes, for example, a lower alkyl halide, lower alkenyl halide, hydroxy(lower) alkyl halide, carboxy(lower)alkyl halide, carbamoyl(lower) alkyl halide, lower alkanoyl(lower)alkyl halide, lower alkoxy(lower)alkyl halide, lower alkoxycarbonyl(lower) alkyl halide, amino(lower)alkyl halide, lower alkylamino (lower)alkyl halide, di(lower)alkylamino(lower)alkyl halide, sulfo(lower)alkyl halide, etc. The above various halides include chlorides, bromides, iodides, etc.

The pyridine derivatives of the formulas (9), (13) and (15) are in tautomerism equilibrium depending on the linkage position of thiol group. For example, the tautomerism of the pyridine derivative of the formula (15) is as represented below. Such isomers are included in the same compound. The pyridine derivatives of the formulas (9), (13) and (15) including such tautomers may be represented by one isomer for convenience but include the other isomer without mentioning it.

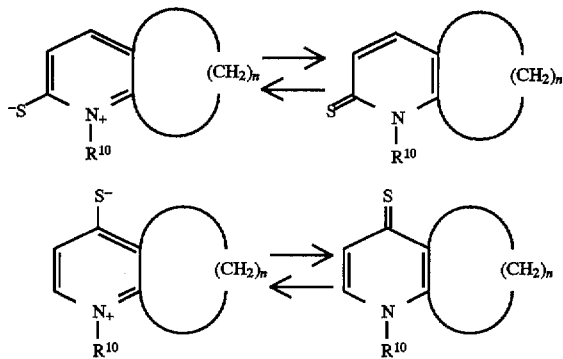

wherein $R^{10}$ and n are as defined hereinbefore.

The compound of this invention is formulated with suitable pharmaceutical carriers in the per se known manner to provide a pharmaceutical composition. As the carriers mentioned above, a variety of substances which are commonly used in pharmaceutical formulation, such as excipients, binders, disintegrators, lubricants, coloring agents, flavoring agents and other corrigents, surfactants, etc., can be mentioned.

There is no limitation on the dosage form in which the pharmaceutical composition of this invention can be administered for the treatment of infections, particularly infections caused by methicillin-resistant strains of Staphylococcus aureus, in man and other mammalian animals but a suitable dosage form can be chosen according to the objective of therapy. Thus, non-peroral dosage forms such as injections, suppositories, eyedrops, ointments, aerosols, etc., and per-oral dosage forms such as tablets, coated tablets, powders, granules, capsules, solutions, pills, suspensions and emulsions can be mentioned.

The above-mentioned dosage forms are manufactured by the pharmaceutical procedures known in this field. Peroral dosage forms such as tablets, powders, granules, etc. can be manufactured using, as said carriers, a variety of excipients such as lactose, sucrose, sodium chloride, glucose, urea, starch, calcium carbonate, kaolin, crystalline cellulose, silicic acid, methylcellulose, glycerin, sodium alginate, gum arabic, etc., binders such as simple syrup, glucose syrup, starch solution, gelatin solution, polyvinyl alcohol, polyvinyl ether, polyvinylpyrrolidone, carboxymethylcellulose, shellac, methylcellulose, ethylcellulose, water, ethanol, potassium phosphate, etc., disintegrators such as dried starch, sodium alginate, agar powder, laminaran powder, sodium hydrogen carbonate, calcium carbonate, polyoxyethylene sorbitan fatty acid esters, sodium lauryl sulfate, stearic acid monoglyceride, starch, lactose, etc., disintegration inhibitors such as sucrose, stearic acid, cacao butter, hydrogenated oil, etc., absorption promoters such as quaternary ammonium bases, sodium lauryl sulfate, etc., humectants such as glycerin, starch, etc., adsorbents such as starch, lactose, kaolin, bentonite, colloidal silica, etc. and lubricants such as purified talc, stearates, boric acid powder, polyethylene glycol, etc. If necessary, tablets may be coated or otherwise covered to provide dragees, gelatin-coated tablets, enteric tablets, film-coated tablets, double-layer tablets, multi-layer tablets and so on.

Pills can be manufactured by using, as carriers, various excipients such as glucose, lactose, starch, cacao butter, hydrogenated vegetable oil, kaolin, talc, etc., binders such as gum arabic powder, gum tragacanth powder, gelatin, etc. and disintegrators such as laminaran, agar and so on.

Capsules can be manufactured by blending the compound with various carriers such as those mentioned above and filling the resultant mixture into hard gelatin capsule shells or soft capsule shells.

Suppositories can be molded by using, as carriers, polyethylene glycol, cacao butter, lanolin, higher alcohols, higher alcohol esters, gelatin, semisynthetic glycerides, Witepsols (registered trademark of Dynamit Nobel), etc. together with suitable absorption promoters. In processing the composition into injections, various diluents such as water, ethyl alcohol, macrogols, propylene glycol, ethoxylated isostearyl alcohol, polyoxylated isostearyl alcohol, polyoxyethylene-sorbitan fatty acid ester, etc., pH control agents and buffers such as sodium citrate, sodium acetate, sodium phosphate, etc., and stabilizers such as sodium pyrosulfite, ethylenediaminetetracetic acid, thioglycolic acid, thiolactic acid, etc. can be used as carriers. The pharmaceutical composition may contain sodium chloride, glucose or glycerin in a sufficient amount to make it isotonic. The conventional solubilizers, soothing agents, local anesthetics, etc. can also be incorporated. After addition of such carriers, a subcutaneous, intramuscular or intravenous injection can be manufactured by the per se known procedures.

The liquid composition may take such forms as aqueous or oil suspensions, solutions, syrups, elixirs and so on. These preparations can be manufactured using the conventional additives in the conventional manner.

The ointment, e.g. a paste, a cream or a gel, can be manufactured using a diluent such as white petrolatum, paraffin, glycerin, cellulose derivatives, polyethylene glycol, silicone, bentonite and so on.

The amount of the compound of this invention in the above-mentioned composition is dependent on dosage form, route of administration and therapeutic regimen and can not, therefore, be specifically stated. However, it can be properly selected from a broad range. Generally speaking, the compound is used in a proportion of about 1 to about 70 weight %.

The route of administration of the composition is not limited to the enteric, peroral, rectal, buccal and transdermal routes but can be selected according to dosage form, patient's age and sex and other background factors, degree or severity of illness and so on. For example, the tablets, pills, solutions, suspensions, emulsions, granules and capsules are administered perorally. The injections can be administered intravenously as they are or in admixture with infusions such as glucose, amino acid and other infusions or, if necessary, intramuscularly, intradermally, subcutaneously or intraperitoneally as they are. The suppositories are administered rectally. The ointments are applied to the skin or the oral mucosa, for instance.

The dosage of the compound of this invention can be selected according to the dosage form, patient's age and clinical condition, type of disease, and species of the compound. Generally speaking, about 100 mg to 10 g a day, or a larger dose, is administered to each patient. For the treatment of infectious diseases caused by pathogenic microorganisms, the daily average dose of about 50 mg, 100 mg, 250 mg, 1000 mg or 2000 mg can be administered.

BEST MODE FOR CARRYING OUT THE INVENTION

Test for antimicrobial activity

To confirm the usefulness of the objective compound of this invention, the antibacterial activities of some representative species of the compound were determined by the agar plate dilution assay and the minimal inhibitory concentration (MIC) values against various bacteria were compared with those of FMOX (flomoxef). The results are shown in Table 1. Moreover, the $MIC_{80}$ values against clinically isolated methicillin-resistant and highly ciprofloxacin-resistant *Staphylococcus aureus* strains were compared with those of VCM (vancomycin), FMOX and CPFX (ciprofloxacin). The results are shown in Table 2. The test compounds were as follows.

Test compounds (a) Chloride 7-[2-cyclopentyloxyimino-2-(2-aminothiazol-4-yl)-acetamido]-3-[2-(1-(2-trimethylammonioethyl)-4-pyridinio)thiovinyl]-3-cephem-4-carboxylate (b) Chloride 7-[2-hydroxyimino-2-(2-aminothiazol-4-yl)acetamido]-3-[2-(1-(2-trimethylammonioethyl)-4-pyridinio)thiovinyl]-3-cephem-4-carboxylate (c) Chloride 7-[2-hydroxyimino-2-(2-aminothiazol-4-yl)acetamido]-3-[2-[1-(2-carbamoylmethyldimethylammonioethyl)-4-pyridinio)thiovinyl]-3-cephem-4-carboxylate (d) Chloride 7-[2-hydroxyimino-2-(2-aminothiazol-4-yl)acetamido]-3-[2-(1-(2-acetonyldimethylammonioethyl)-4-pyridinio)thiovinyl]-3-cephem-4-carboxylate (e) Chloride 7-[2-hydroxyimino-2-(2-aminothiazol-4-yl)acetamido]-3-[2-(1-(2-hydroxyethyldimethylammonioethyl)-4-pyridinio)thiovinyl]-3-cephem-4-carboxylate (f) Chloride 7-[2-hydroxyimino-2-(2-aminothiazol-4-yl)-acetamido]-3-[2-(1-(2-(4-methylmorpholinio)ethyl)-4-pyridinio)thiovinyl]-3-cephem-4-carboxylate

TABLE 1

| MIC value (µg/ml) | Inoculum size: $10^6$ cells/ml | | | |
|---|---|---|---|---|
| | Test compound | | | |
| Organism | (a) | (b) | (c) | (d) |
| S. aureus FDA 209-P | 0.39 | 0.1 | 0.1 | 0.2 |
| E. faecalis ATCC-21212 | 0.39 | 0.1 | 0.1 | 0.2 |
| MRSA 92-1044 | 6.25 | 1.56 | 1.56 | 1.56 |
| E. coli NIHJ JC-2 | 0.39 | 0.05 | 0.025 | 0.025 |
| S. marcescens IFO-12648 | 3.13 | 0.1 | 0.1 | 0.2 |
| | Test compound | | | |
| Organism | (e) | (f) | FMOX | |

TABLE 1-continued

| MIC value (µg/ml) | Inoculum size: $10^6$ cells/ml | | |
|---|---|---|---|
| S. aureus FDA 209-P | 0.1 | 0.1 | 0.2 |
| E. faecalis ATCC-21212 | 0.1 | 0.2 | 100 |
| MRSA 92-1044 | 1.56 | 1.56 | >100 |
| E. coli NIHJ JC-2 | 0.05 | 0.025 | 0.05 |
| S. marcescens IFO-12648 | 0.1 | 0.1 | 0.2 |

TABLE 2

$MIC_{80}$ values against clinically isolated methicillin-resistant, highly ciprofloxacin-resistant *Staphylococcus aureus* strains

| MIC-80 value (µg/ml) | Inoculum size: $10^6$ cells/ml | | | | | |
|---|---|---|---|---|---|---|
| | Test compound | | | | | |
| Organism | (b) | (c) | (e) | VCM | FMOX | CPFX |
| MRSA(DMPPC;MIC ≧ 12.5 µg/ml) | 1.56 | 1.56 | 3.13 | 1.56 | 100 | 100 |
| MRSA(CPFX;MIC ≧ 100 µg/ml) | 1.56 | 1.56 | 3.13 | 1.56 | 100 | >100 |

Examples are given below.

EXAMPLE 1

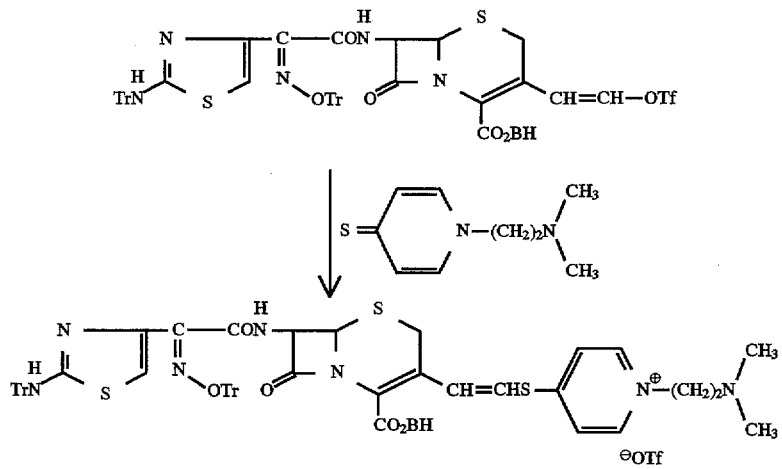

wherein Tr represents a trityl group, BH represents a benzhydryl group and Tf represents a trifluoromethane sulfonyl group; the same applies hereinafter.

A 19.7 g (0.0165 mol) quantity of benzhydryl 7-[2-trityloxyimino-2-(2-tritylaminothiazol-4-yl)acetamido]-3-(2-trifluoromethanesulfonyloxyvinyl)-3-cephem-4-carboxylate and 3.16 g (0.017 mol) of 1-(2-dimethylaminoethyl)-4-pyridothion were dissolved in 150 ml of anhydrous dimethylformamide. The resultant solution was stirred at room temperature for 2.5 hours. After completion of the reaction, the reaction mixture was extracted with ethyl acetate (1200 ml), and washed with water three times and with a 10% aqueous solution of sodium chloride once. The organic layer was dried over anhydrous magnesium sulfate. The organic solvent was distilled off under reduced pressure to give 20.3 g of the contemplated product, i.e. benzhydryl 7-[2-trityloxyimino-2-(2-tritylaminothiazol-4-yl)acetamido]-3-[2-(1-(2-dimethylaminoethyl)-4-pyridinio) thiovinyl]-3-cephem-4-carboxylate trifluoromethane sulfonate.

$^1$H-NMR(DMSO-d$_6$) δppm; 2.15 (6H, s), 2.69 (2H, m), 3.77 (1H, ABq, J=17.1 Hz), 4.18 (1H, ABq, J=17.1 Hz), 4.55 (2H, m), 5.35 (1H, d, J=4.8 Hz), 5.98 (1H, dd, J=4.8 Hz, 7.8 Hz), 6.63 (1H, s), 6.97 (1H, s), 7.1–7.6 (42H, m), 8.09 (2H, d, J=6.9 Hz), 8.75 (2H, d, J=6.9 Hz), 8.79 (1H, s), 9.93 (1H, d, J=7.8 Hz)

EXAMPLE 2

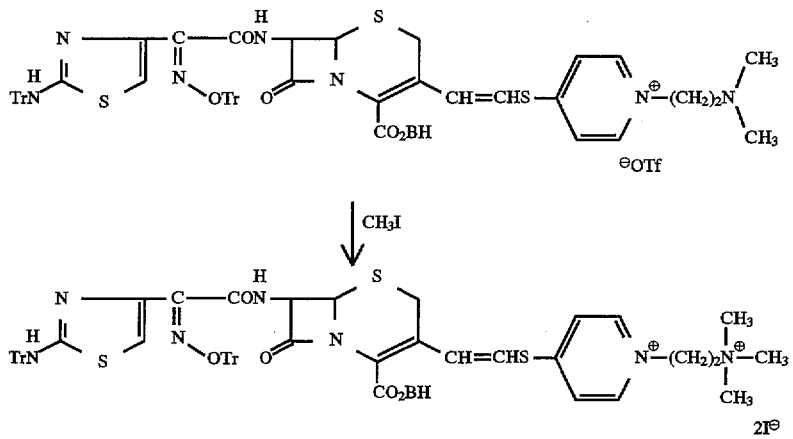

In 100 ml of acetonitrile was dissolved 20.3 g (0.016 mol) of benzhydryl 7-[2-trityloxyimino-2-(2-tritylaminothiazol-4-yl)acetamido]-3-[2-(1-(2-dimethylaminoethyl)-4-pyridinio)thiovinyl]-3-cephem-4-carboxylate trifluoromethane sulfonate. To the solution was added 10.3 ml (0.16 mol) of methyl iodide. The mixture was stirred at room temperature for 2 hours. After completion of the reaction, the solvent was distilled off under reduced pressure, giving 22.6 g of benzhydryl 7-[2-trityloxyimino-2-(2-tritylaminothiazol-4-yl)acetoamide]-3-[2-(1-(2-trimethylammonioethyl)-4-pyridinio)thiovinyl]-3-cephem-4-carboxylate iodide.

$^1$H-NMR(DMSO-d$_6$) δppm; 3.15 (9H, s), 3.77 (1H, ABq, J=17.1 Hz), 3.91 (2H, m), 4.18 (1H, ABq, J=17.1 Hz), 4.96 (2H, m), 5.35 (1H, d, J=4.8 Hz), 5.98 (1H, dd, J=4.8 Hz, 7.8 Hz), 6.62 (1H, s), 6.97 (1H, s), 7.1–7.6 (42H, m), 8.20 (2H, d, J=6.9 Hz), 8.79 (1H, brs), 8.82 (2H, d, J=6.9 Hz), 9.93 (1H, d, J=7.8 Hz)

EXAMPLE 3

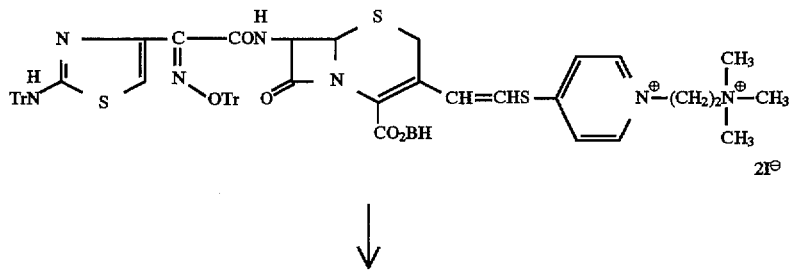

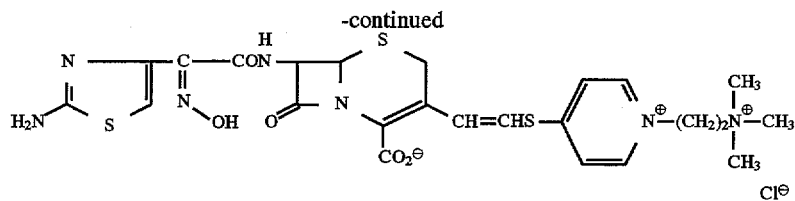
-continued

In 70 ml of chloroform was dissolved 22.6 g (0.016 mol) of benzhydryl 7-[2-trityloxyimino-2-(2-tritylaminothiazol-4-yl)acetoamide]-3-[2-(1-(2-trimethylammonioethyl)-4-pyridinio)thiovinyl]-3-cephem-4-carboxylate iodide. To the solution were added 40 ml of 88% formic acid and 5.5 ml of concentrated hydrochloric acid. The mixture was stirred at room temperature for 4 hours. After completion of the reaction, the formic acid layer was washed with chloroform (70 ml, three times). The mixture was added dropwise to isopropyl ether/acetone (200 ml/600 ml). The obtained precipitate was collected by filtration, giving 7.0 g of a crude product of 7-[2-hydroxyimino-2-(2-aminothiazol-4-yl)acetamido]-3-[2-(1-(2-trimethylammonioethyl)-4-pyridinio)thiovinyl]-3-cephem-4-carboxylate. The crude product was dissolved in 130 ml of 0.1N hydrochloric acid, and the solution was adsorbed on a column using a hyperporous polymer (Mitsubishi Kasei Corp., Diaion HP-21). Elution was carried out with water and with water/acetonitrile. The fractions containing the desired compound were collected, concentrated under reduced pressure and lyophilized to give 3.0 g of chloride 7-[2-hydroxyimino-2-(2-aminothiazol-4-yl)acetoamide]-3-[2-(1-(2-trimethylammonioethyl)-4-pyridinio)thiovinyl]-3-cephem-4-carboxylate.

$^1$H-NMR(DMSO-$d_6$) $\delta$ppm; 3.18 (9H, s), 3.59 (1H, ABq, J=17.1 Hz), 3.87 (1H, ABq, J=17.1 Hz), 4.00 (2H, m), 5.04 (2H, m), 5.13 (1H, d, J=4.8 Hz), 5.70 (1H, dd, J=4.8 Hz, 7.8 Hz), 6.64 (1H, s), 6.6–6.8 (1H, m), 7.13 (2H, m), 7.42 (1H, d, J=15.3 Hz), 8.12 (2H, d, J=6.6 Hz), 8.96 (2H, d, J=6.6 Hz), 9.45 (1H, d, J=7.8 Hz), 11.38 (1H, s)

EXAMPLE 4

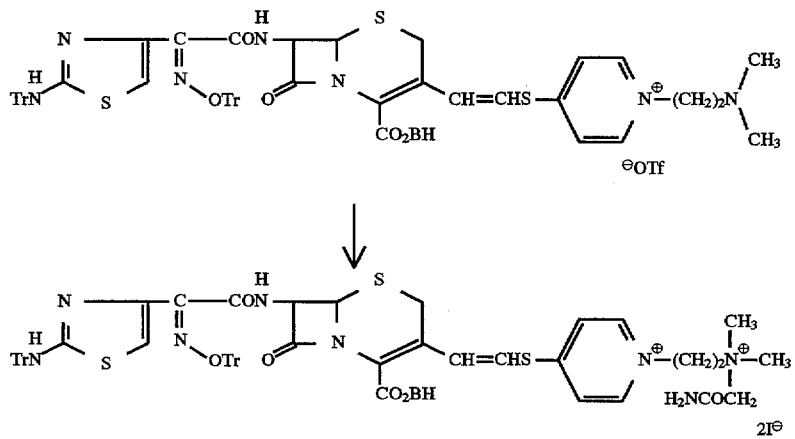

A 1.8 g (0.098 mol) quantity of 2-iodoacetamido was added to a solution of 3.0 g (0.0024 mol) of benzhydryl 7-[2-trityloxyimino-2-(2-tritylaminothiazol-4-yl)acetamido]-3-[2-(1-(2-dimethylaminoethyl)-4-pyridinio)thiovinyl]-3-cephem-4-carboxylate trifluoromethane sulfonate in 15 ml of acetonitrile. The mixture was stirred at room temperature for 4 hours. After completion of the reaction, the solvent was distilled off under reduced pressure, giving 4.8 g of a mixture of benzhydryl 7-[2-trityloxyimino-2-(2-tritylaminothiazol-4-yl)acetoamide]-3-[2-(1-(2-carbamoylmethyl-dimethylammonioethyl)-4-pyridinio)thiovinyl]-3-cephem-4-carboxylate iodide and 2-iodoacetoamide.

$^1$H-NMR(DMSO-$d_6$) δppm; 3.15 (6H, s), 3.75 (1H, ABq, J=17.1 Hz), 4.1–4.2 (5H, m), 4.97 (2H, m), 5.35 (1H, d, J=5.1 Hz), 5.98 (1H, dd, J=5.1 Hz, 8.1 Hz), 6.62 (1H, s), 6.95 (1H, s), 7.0–8.0 (44H, m), 8.18 (2H, d, J=6.6 Hz), 8.78 (1H, s), 8.86 (2H, d, J=6.6 Hz), 9.92 (1H, d, J=8.1 Hz)

EXAMPLE 5

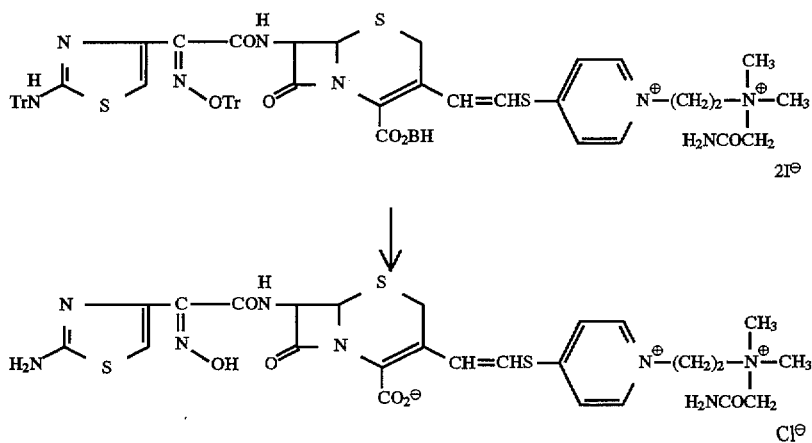

A solution of 4.8 g of benzhydryl 7-[2-trityloxyimino-2-(2-tritylaminothiazol-4-yl)acetamido]-3-[2-(1-(2-carbamoylmethyl-dimethylammoniethyl-4-pyridinio)thiovinyl]-3-cephem-4-carboxylate iodide in 8 ml of chloroform was admixed with 6 ml of 88% formic acid and 0.8 ml of concentrated hydrochloric acid. The mixture was stirred at room temperature for 3.5 hours. After completion of the reaction, the formic acid layer was washed with chloroform (8 ml, 3 times). The mixture was added dropwise to isopropyl ether/acetone (50 ml/100 ml). The obtained precipitate was collected by filtration, giving 1.4 g of a crude product of 7-[2-hydroxyimino-2-(2-aminothiazol-4-yl)acetamido]-3-[2-(1-(2-carbamoylmethyl-dimethylammonioethyl)-4-pyridinio)thiovinyl]-3-cephem-4-carboxylate. The crude product was dissolved in 14 ml of water. The solution was adsorbed on a column using a hyperporous polymer (Mitsubishi Kasei Corp., Diaion HP-21), and elution was carried out with water and with water/acetonitrile. The fractions containing the contemplated compound were collected, concentrated under reduced pressure and lyophilized to give 327 mg of chloride 7-[2-hydroxyimino-2-(2-aminothiazol-4-yl)acetoamide]-3-[2-(1-(2-carbamoylmethyl-dimethylammonioethyl)-4-pyridinio)thiovinyl]-3-cephem-4-carboxylate.

$^1$H-NMR(DMSO-$d_6$) δppm; 3.34 (6H, s), 3.60 (1H, ABq, J=17.1 Hz), 3.92 (1H, ABq, J=17.1 Hz), 4.21 (2H, m), 4.29 (2H, s), 5.11 (2H, m), 5.13 (1H, d, J=5.1 Hz), 5.72 (1H, dd, J=5.1 Hz, 8.1 Hz), 6.65 (1H, s), 6.6–6.8 (1H, m), 7.12 (2H, brs), 7.40 (1H, d, J=15.0 Hz), 7.72 (1H, brs), 8.19 (2H, d, J=6.6 Hz), 8.32 (1H, brs), 8.97 (2H, d, J=6.6 Hz), 9.44 (1H, d, J=8.1 Hz), 11.38 (1H, s)

EXAMPLE 6

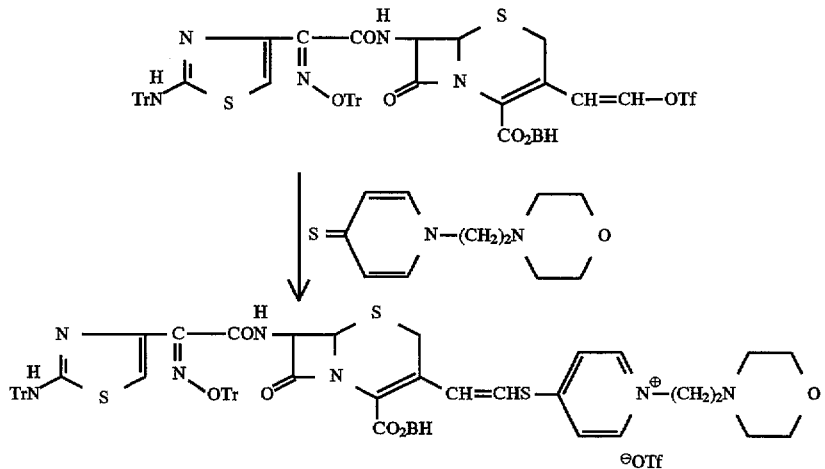

A solution of benzhydryl 7-[2-trityloxyimino-2-(2-tritylaminothiazol-4-yl)acetamido]-3-(2-trifluoromethanesufonyloxyvinyl)-3-cephem-4-carboxylate (15.7 g, 0.0132 mol) and 3.1 g (0.014 mol) of 1-(2-morpholinoethyl)-4-pyridothion in 80 ml of anhydrous dimethylformamide was stirred at room temperature for 2.5 hours. After completion of the reaction, the reaction mixture was extracted with ethyl acetate (800 ml) and washed with water twice and with a 10% aqueous solution of sodium chloride twice. The organic layer was dried over anhydrous magnesium sulfate after which the organic solvent was distilled off under reduced pressure, giving 13.1 g of the contemplated product, i.e. benzhydryl 7-[2-trityloxyimino-2-(2-tritylaminothiazol-4-yl)acetamido]-3-[2-(1-(2-morpholinoethyl)-4-pyridinio)thiovinyl]-3-cephem-4-carboxylate trifluoromethane sulfonate.

$^1$H-NMR(DMSO-$d_6$) δppm; 2.41 (4H, m), 2.75 (2H, m), 3.48 (4H, m), 3.76 (1H, ABq, J=18.0 Hz), 4.16 (1H, ABq, J=18.0 Hz), 4.55 (2H, m), 5.35 (1H, d, J=4.8 Hz), 5.97 (1H, dd, J=4.8 Hz, 7.8 Hz), 6.63 (1H, s), 6.99 (1H, s), 7.1–7.6 (42H, m), 8.07 (2H, d, J=7.2 Hz), 8.72 (2H, d, J=7.2 Hz), 8.77 (1H, s), 9.93 (1H, d, J=7.8 Hz)

EXAMPLE 7

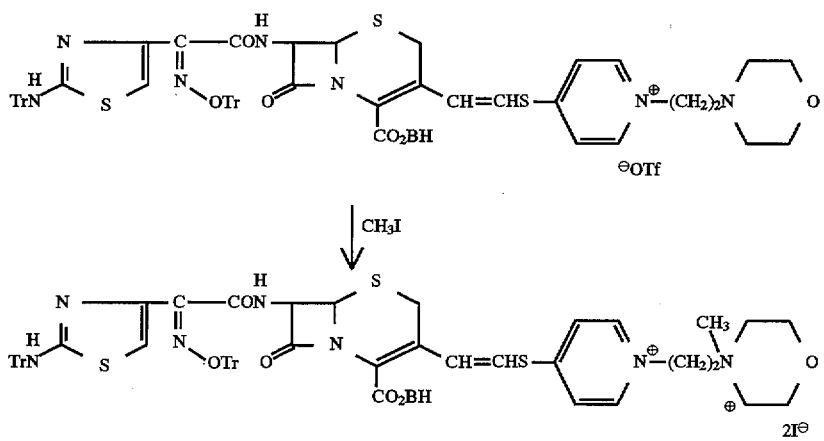

A 10 ml (0.16 ml) quantity of methyl iodide was added to 2 g (0.0016 mol) of benzhydryl 7-[2-trityloxyimino-2-(2-tritylaminothiazol-4-yl)acetamido]-3-[2(1-(2-morpholinoethyl)-4-pyridinio)thiovinyl]-3-cephem-4-carboxylate trifluoromethane sulfonate. The mixture was stirred at room temperature for 64 hours. After completion of the reaction, the methyl iodide was distilled off under reduced pressure, giving 2.15 g of benzhydryl 7-[2-trityloxyimino-2-(2-tritylaminothiazol-4-yl)acetamido]-3-[2-(1-(2-(4-methylmorpholinio)ethyl)-4-pyridinio)thiovinyl]-3-cephem-4-carboxylate iodide.

$^1$H-NMR(DMSO-$d_6$) δppm; 3.28 (3H, s), 3.52 (4H, m), 3.77 (1H, ABq, J=18.0 Hz), 3.96 (4H, m), 4.07 (2H, m), 4.18 (1H, ABq, J=18.0 Hz), 4.99 (2H, m), 5.35 (1H, d, J=5.1 Hz), 5.98 (1H, dd, J=5.1 Hz, 8.4 Hz), 6.63 (1H, s), 6.98 (1H, s), 7.1–7.6 (42H, m), 8.21 (2H, d, J=6.9 Hz), 8.78 (1H, s), 8.87 (2H, d, J=6.9 Hz), 9.94 (1H, d, J=8.4 Hz)

EXAMPLE 8

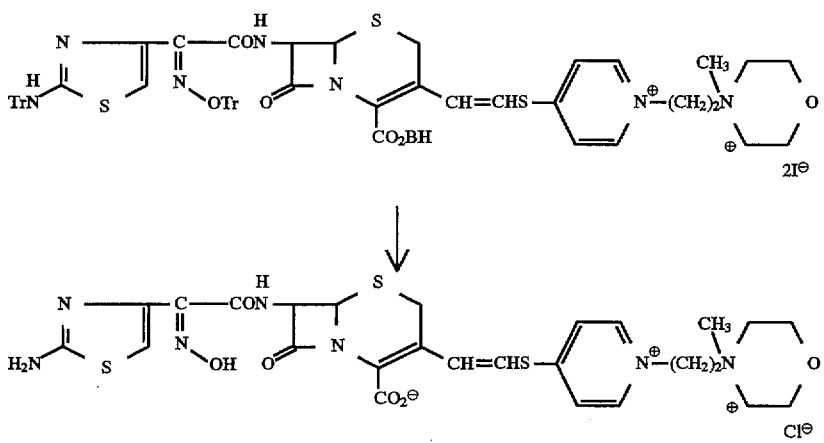

To a solution of benzhydryl 7-[2-trityloxyimino-2-(2-tritylaminothiazol-4-yl)acetamido]-3-[2-(1-(2-(4-methylmorpholinio)ethyl)-4-pyridinio)thiovinyl]-3-cephem-4-carboxylate iodide (2.1 g) in 5 ml of chloroform were added 3.2 ml of 88% formic acid and 0.496 ml of concentrated hydrochloric acid. The mixture was stirred at room temperature for 4 hours. After completion of the reaction, the formic acid layer was washed with chloroform (5 ml, three times). The mixture was added dropwise to isopropyl ether/acetone (20 ml/50 ml). The obtained precipitate was collected by filtration, giving 0.55 g of a crude product of 7-[2-hydroxyimino-2-(2-aminothiazol-4-yl) acetamido]-3-[2-(1-(2-(4-methylmorpholinio)ethyl)-4-pyridinio)thiovinyl]-3-cephem-4-carboxylate. The crude product was dissolved in 5 ml of 0.1N hydrochloric acid, and the solution was adsorbed on a column using a hyperporous polymer (Mitsubishi Kasei Corp., Diaion HP-21). Elution was carried out with water and with water/acetonitrile. The fractions containing the desired compound were collected, concentrated under reduced pressure and lyophilized to give 0.156 g of chloride 7-[2-hydroxyimino-2-(2-aminothiazol-4-yl)acetoamide]-3-2-(1-(2-(4-methylmorpholinio)ethyl)-4-pyridinio)thiovinyl]-3-cephem-4-carboxylate.

$^1$H-NMR(DMSO-$d_6$) δppm; 3.30 (3H, s), 3.53 (4H, m), 3.61 (1H, ABq, J=16.8 Hz), 3.95 (6H, m), 4.01 (2H, m), 5.02 (2H, m), 5.15 (1H, d, J=5.1 Hz), 5.73 (1H, dd, J=5.1 Hz, 8.4 Hz), 6.66 (1H, s), 6.80 (1H, m), 7.11 (2H, m), 7.41 (1H, d, J=15.0 Hz), 8.15 (2H, d, J=6.9 Hz), 8.91 (2H, d, J=6.9 Hz), 9.46 (1H, d, J=8.4 Hz), 11.32 (1H, s)

EXAMPLE 9

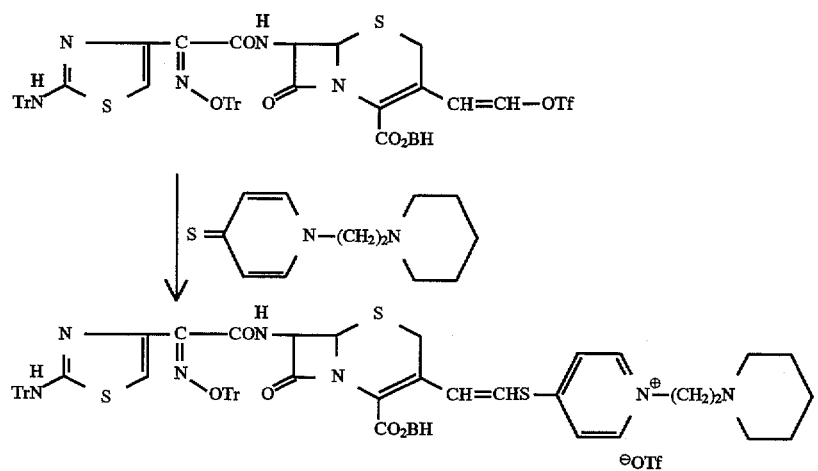

A solution of 2.0 g of benzhydryl 7-[2-trityloxyimino-2-(2-tritylaminothiazol-4-yl)acetamido]-3-(2-trifluoromethanesulfonyloxyvinyl)-3-cephem-4-carboxylate and 0.4 g of 1-(2-piperidinoethyl)-4-pyridothion in 10 ml of anhydrous dimethylformamide was stirred at room temperature for 4 hours. After completion of the reaction, the reaction mixture was extracted with ethyl acetate (100 ml), and washed with water twice and with a 10% aqueous solution of sodium chloride twice. The organic layer was dried over anhydrous magnesium sulfate. The organic solvent was distilled off under reduced pressure. The residue was dissolved in 10 ml of chloroform. The solution was added dropwise to 100 ml of isopropyl ether to produce a precipitate. The precipitate was recovered by filtration and dried to give 1.99 g of the contemplated product, i.e.

benzhydryl 7-[2-trityloxyimino-2-(2-tritylaminothiazol-4-yl)acetamido]-3-[2-(1-(2-piperidinoethyl)-4-pyridinio)thiovinyl]-3-cephem-4-carboxylate trifluoromethane sulfonate.

$^{1}$H-NMR(DMSO-d$_6$) δppm; 1.3–1.5 (6H, m), 2.3–2.4 (4H, m), 2.7 (2H, m), 3.75 (1H, ABq, J=17.1 Hz), 4.15 (1H, ABq, J=17.1 Hz), 4.5 (2H, m), 5.32 (1H, d, J=4.8 Hz), 5.97 (1H, dd, J=4.8 Hz, 8.2 Hz), 6.61 (1H, s), 6.98 (1H, s), 7.0–7.6 (42H, m), 8.05 (2H, d, J=6.9 Hz), 8.68 (2H, d, J=6.9 Hz), 9.93 (1H, d, J=8.2 Hz)

EXAMPLE 10

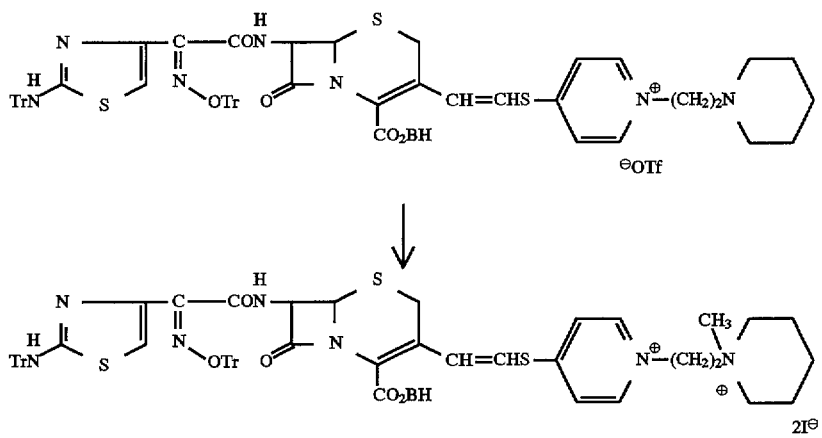

In 6 ml of acetonitrile was dissolved 2 g of benzhydryl 7-[2-trityloxyimino-2-(2-tritylaminothiazol-4-yl) acetoamido]-3-[2-(1-(2-piperidinoethyl)-4-pyridinio) thiovinyl]-3-cephem-4-carboxylate trifluoromethane sulfonate. To the solution was added 2.6 ml of methyl iodide. The mixture was stirred at room temperature for 16 hours. After completion of the reaction, the reaction mixture was added dropwise to 86 ml of isopropyl ether to produce a precipitate. The precipitate was collected by filtration and dried to provide 1.93 g of benzhydryl 7-[2-trityloxyimino-2-(2-tritylaminothiazol-4-yl)acetoamido]-3-[2-(1-(2-(1-methylpiperidinio)ethyl)-4-pyridinio)thiovinyl]-3-cephem-4-carboxylate iodide.

$^{1}$H-NMR(DMSO-d$_6$) δppm; 1.5–1.6 (2H, m), 1.7–1.9 (4H, m), 3.15 (3H, s), 3.3–3.5 (4H, m), 3.77 (1H, ABq, J=17.1 Hz), 3.9–4.0 (2H, m), 4.18 (1H, ABq, J=17.1 Hz), 4.9–5.0 (2H, m), 5.35 (1H, d, J=4.8 Hz), 5.98 (1H, dd, J=4.8 Hz, 8.2 Hz), 6.62 (1H, s), 6.99 (1H, s), 7.0–7.6 (42H, m), 8.2 (2H, d, J=6.9 Hz), 8.87 (2H, d, J=6.9 Hz), 9.92 (1H, d, J=8.2 Hz)

EXAMPLE 11

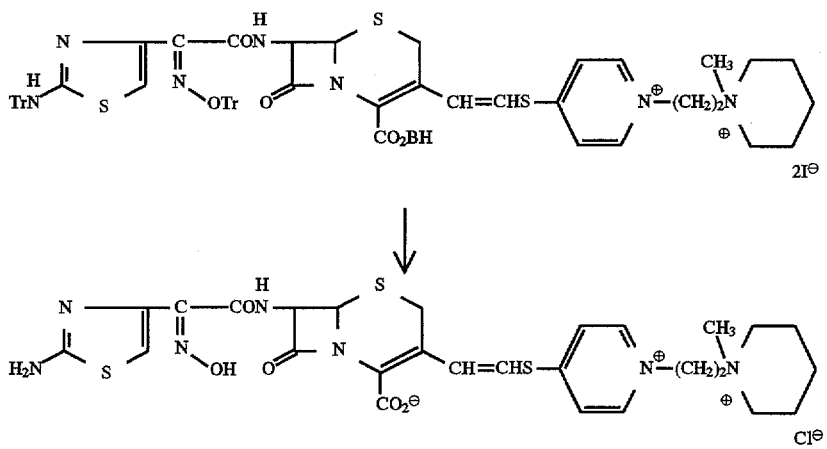

A solution of 1.8 g of benzhydryl 7-[2-trityloxyimino-2-(2-tritylaminothiazol-4-yl)acetamido]-3-[2-(1-(2-(1-methylpiperidinio)ethyl)-4-pyridinio)thiovinyl]-3-cephem-4-carboxylate iodide in 5.1 ml of chloroform was added to 3.4 ml of 88% formic acid and 0.296 ml of concentrated hydrochloric acid. The mixture was stirred at room temperature for 3.5 hours. After completion of the reaction, the formic acid layer was washed with chloroform (5 ml, 3 times). The mixture was added dropwise to isopropyl ether/ acetone (8.5 ml/31 ml). The obtained precipitate was collected by filtration, giving 0.65 g of a crude product of 7-[2-hydroxyimino-2-(2-aminothiazol-4-yl)acetamido]-3-[2-(1-(2-(1-methylpiperidinio)ethyl)-4-pyridinio)thiovinyl]-3-cephem-4-carboxylate. The crude product was dissolved in water. The solution was adsorbed on a column using a hyperporous polymer (Mitsubishi Kasei Corp., Diaion HP-21) and elution was carried out with water and with water/acetonitrile. The fractions containing the desired compound were collected, concentrated under reduced pressure and lyophilized to give 0.273 g of chloride 7-[2-hydroxyimino-2-(2-aminothiazol-4-yl)acetoamido]-3-[2-(1-(2-(1-methylpiperidinio)ethyl)-4-pyridinio)thiovinyl]-3-cephem-4-carboxylate.

$^1$H-NMR(DMSO-$d_6$) δppm; 1.4–1.6 (2H, m), 1.7–1.9 (4H, m), 3.19 (3H, s), 3.3–3.5 (4H, m), 3.58 (1H, d, J=17.1 Hz), 3.85 (1H, d, J=17.1 Hz), 4.0–4.1 (2H, m), 5.0–5.1 (2H, m), 5.12 (1H, d, J=4.8 Hz), 5.70 (1H, dd, J=4.8 Hz,8.2 Hz), 6.63 (1H, d, J=15.3 Hz), 6.65 (1H, s), 7.15 (2H, brs), 7.41 (1H, d, J=15.3 Hz), 8.08 (2H, d, J=6.9 Hz), 9.00 (2H, d, J=6.9 Hz), 9.45 (1H, d, J=8.2 Hz), 11.48 (1H, s)

EXAMPLE 12

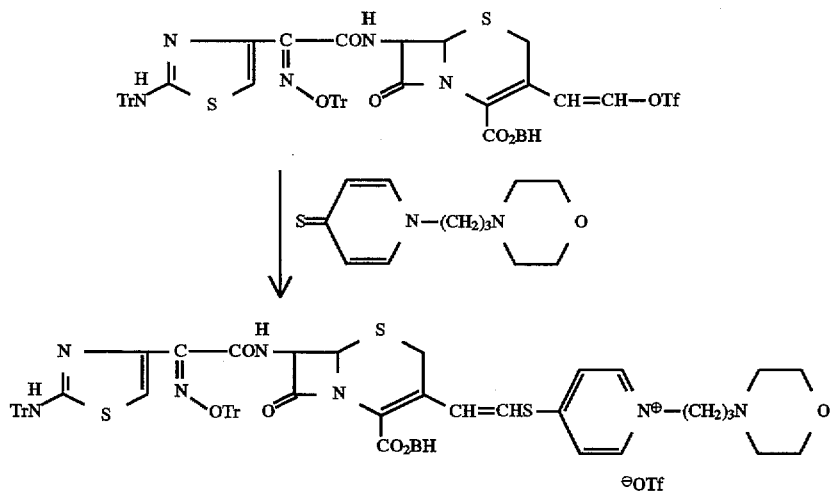

In 10 ml anhydrous dimethylformamide were dissolved 3.28 g of benzhydryl 7-[2-trityloxyimino-2-(2-tritylaminothiazol-4-yl)acetamido]-3-[2-trifluoromethanesulfonyloxyvinyl)-3-cephem-4-carboxylate and 0.73 g of 1-(3-morpholinopropyl)-4-pyridothion. The solution was stirred at room temperature for 62.5 hours. After completion of the reaction, the reaction mixture was extracted with 100 ml of ethyl acetate and washed with water twice and with a 10% aqueous solution of sodium chloride twice. The organic layer was dried over anhydrous magnesium sulfate after which the organic solvent was distilled off under reduced pressure. The residue was dissolved in 15 ml of chloroform. Then the solution was added dropwise to 700 ml of isopropyl ether to give a precipitate. The precipitate was recovered by filtration and dried to provide 2.8 g of the contemplated product, i.e. benzhydryl 7-[2-trityloxyimino-2-(2-tritylaminothiazol-4-yl)acetamido]-3-[2-(1-(3-morpholinopropyl)-4-pyridinio)thiovinyl]-3-cephem-4-carboxylate trifluoromethane sulfonate.

$^1$H-NMR(DMSO-$d_6$) δppm; 2.05 (2H, m), 2.23 (6H, m), 3.43 (4H, brs), 3.74 (1H, d, J=17.4 Hz), 4.17 (1H, d, J=17.4 Hz), 4.48 (2H, brs), 5.36 (1H, d, J=4.8 Hz), 5.96 (1H, dd, J=4.8 Hz, 8.4 Hz), 6.60 (1H, s), 6.96 (1H, s), 7.1–7.6 (42H, m), 8.06 (2H, d, J=6.0 Hz), 8.78 (3H, m), 9.95 (1H, d, J=8.4 Hz)

EXAMPLE 13

A 15 ml quantity of methyl iodide was added to 1.36 g of benzhydryl 7-[2-trityloxyimino-2-(2-tritylaminothiazol-4-yl)acetamido]-3-[2-(1-(3-morpholinopropyl)-4-pyridinio)thiovinyl]-3-cephem-4-carboxylate trifluoromethane sulfonate. The mixture was stirred at room temperature for 16 hours. After completion of the reaction, the solvent was distilled off under reduced pressure, giving 1.4 g of benzhydryl 7-[2-trityloxyimino-2-(2-tritylaminothiazole-4-yl)acetamido]-3-[2-(1-(3-(4-methylmorpholinio)propyl)-4-pyridinio)thiovinyl]-3-cephem-4-carboxylate iodide.

$^1$H-NMR(DMSO-$d_6$) δppm; 2.38 (2H, m), 3.10 (3H, s), 3.40 (4H, m), 3.48 (2H, m), 3.78 (1H, d, J=17.4 Hz), 3.92 (4H, brs), 4.19 (1H, d, J=17.4 Hz), 4.53 (2H, brs), 5.37 (1H, d, J=4.8 Hz), 5.98 (1H, dd, J=4.8 Hz, 8.4 Hz), 6.61 (1H, s), 6.96 (1H, s), 7.1–7.6 (42H, m), 8.18 (2H, d, J=6.0 Hz), 8.78 (3H, m), 9.95 (1H, d, J=8.4 Hz)

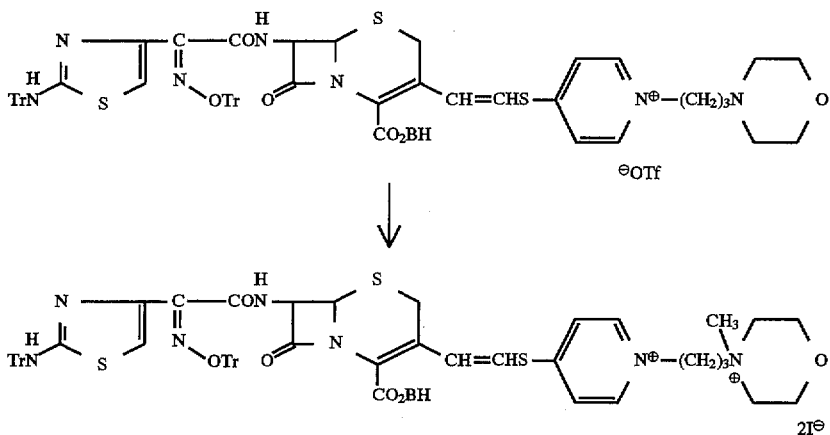

EXAMPLE 14

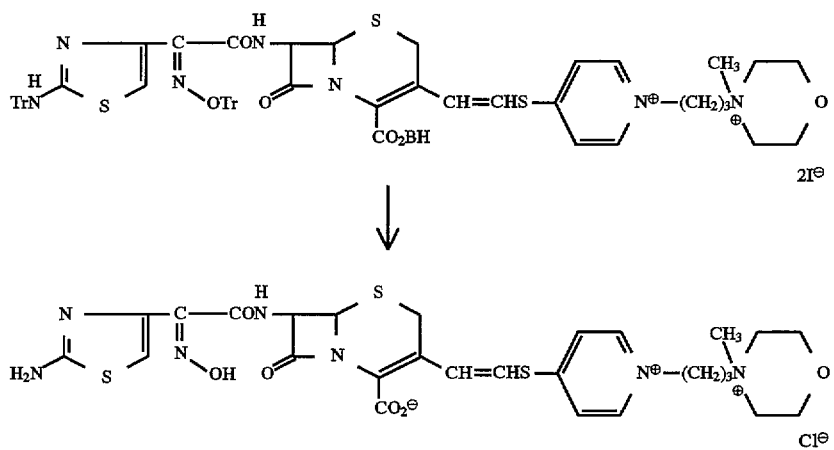

A solution of 1.7 g of benzhydryl 7-[2-trityloxyimino-2-(2-tritylaminothiazol-4-yl)acetamido]-3-2-(1-(3-(4-methylmorpholinio)propyl)-4-pyridinio)thiovinyl]-3-cephem-4-carboxylate iodide in 3.8 ml of chloroform was added to 2.5 ml of 88% formic acid and 0.278 ml of concentrated hydrochloric acid. The mixture was stirred at room temperature for 3.5 hours. After completion of the reaction, the formic acid layer was washed with chloroform (4 ml, 5 times). The mixture was added dropwise to isopropyl ether/acetone (20 ml/40 ml). The obtained precipitate was recovered by filtration, giving 0.53 g of a crude product of 7-[2-hydroxyimino-2-(2-aminothiazol-4-yl)acetamido]-3-[2-(1-(3-(4-methylmorpholinio)propyl)-4-pyridinio)thiovinyl]-3-cephem-4-carboxylate. The crude product was dissolved in water. The solution was adsorbed on a column using a hyperporous polymer (Mitsubishi Kasei Corp., Diaion HP-21), and elution was carried out with water and with water/acetonitrile. The fractions containing the desired compound were collected, concentrated under reduced pressure and lyophilized to give 0.112 g of chloride 7-[2-hydroxyimino-2-(2-aminothiazol-4-yl)acetoamido]-3-[2-(1-(3-(4-methylmorpholinio)propyl)-4-pyridinio)thiovinyl]-3-cephem-4-carboxylate.

$^1$H-NMR(DMSO-$d_6$) δppm; 2.36 (2H, m), 3.09 (3H, s), 3.43 (4H, m), 3.58 (2H, m), 3.75 (1H, d, J=17.4 Hz), 3.92 (4H, brs), 4.20 (1H, d, J=17.4 Hz), 4.58 (2H, brs), 5.23 (1H, d, J=4.8 Hz), 5.83 (1H, dd, J=4.8 Hz, 8.4 Hz), 6.48 (1H, m), 6.63 (1H, s), 7.08 (2H, brs), 7.45 (1H, d, J=15.4 Hz), 8.06 (2H, d, J=6.0 Hz), 8.74 (2H, d, J=6.0 Hz), 9.42 (1H, d, J=8.4 Hz), 11.30 (1H, s)

EXAMPLE 15

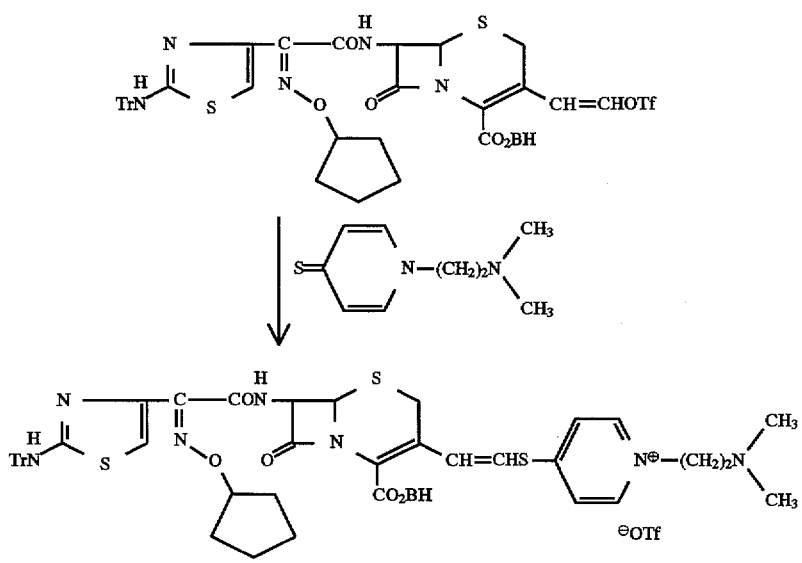

A 1.59 9 quantity of benzhydryl 7-[2-cyclopentyloxyimino-2-(2-tritylaminothiazol-4-yl)acetamido]-3-(2-trifluoromethanesufonyloxyvinyl)-3-cephem-4-carboxylate and 0.3 9 of 1-(2-dimethylaminoethyl)-4-pyridothion were dissolved in 8.0 ml of anhydrous diemthylformamide. The solution was stirred at room temperature for 4.5 hours. After completion of the reaction, the reaction mixture was extracted with ethyl acetate (120 ml) and washed with water three times and with a 10% aqueous solution of sodium chloride once. The organic layer was dried over anhydrous magnesium sulfate after which the organic solvent was distilled off under reduced pressure. The residue was dissolved in 8 ml of chloroform. The solution was added dropwise to 80 ml of diisopropyl ether to give a precipitate. The precipitate was dried to provide 1.43 g of the contemplated product, i.e. benzhydryl 7-[2-cyclopentyloxyimino-2-(2-tritylaminothiazol-4-yl)acetamido]-3-[2-(1-(2-dimethylaminoethyl)-4-pyridinio)thiovinyl]-3-cephem-4-carboxylate trifluoromethane sulfonate.

$^1$H-NMR(DMSO-$d_6$) δppm; 1.4–1.9 (8H, m), 2.15 (6H, s), 2.69 (2H, m), 3.70 (1H, d, J=17.0 Hz), 4.15 (1H, d, J=17.0 Hz), 4.55 (2H, m), 4.63 (1H, m), 5.25 (1H, d, J=5.1 Hz), 5.78 (1H, dd, J=5.1 Hz, 8.4 Hz), 6.65 (1H, s), 6.98 (1H, s), 7.0–7.6 (42H, m), 8.06 (2H, d, J=6.9 Hz), 8.72 (2H, d, J=6.9 Hz), 9.52 (1H, d, J=8.4 Hz)

EXAMPLE 16

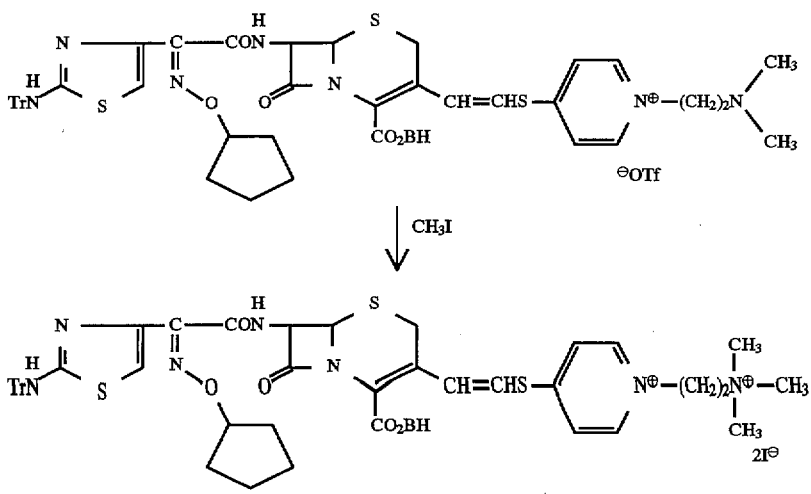

Methyl iodide (0.75 ml) was added to a solution of 1.42 g of benzhydryl 7-[2-cyclopentyloxyimino-2-(2-tritylaminothiazol-4-yl)acetamido]-3-[2-(1-(2-dimethylaminoethyl)-4-pyridinio)thiovinyl]-3-cephem-4-carboxylate trifluoromethane sulfonate in 7.1 ml of acetonitrile. The mixture was stirred at room temperature for 1.5 hours. After completion of the reaction, the reaction mixture was added dropwise to diisoproyl ether to form a precipitate, which was collected by filtration and dried, giving 1.52 g of benzhydryl 7-[2-cyclopentyloxyimino-2-(2-tritylaminothiazol-4-yl)acetamido]-3-[2-(1-(2-trimethylammonioethyl)-4-pyridinio)thiovinyl]-3-cephem-4-carboxylate iodide.

$^1$H-NMR(DMSO-$d_6$) δppm; 1.4–1.9 (8H, m), 3.16 (9H, s), 3.71 (1H, d, J=17.0 Hz), 3.85–3.95 (2H, m), 4.18 (1H, d, J=17.0 Hz), 4.62 (1H, m), 4.9–5.0 (2H, m), 5.27 (1H, d, J=5.1 Hz), 5.78 (1H, dd, J=5.1 Hz, 8.4 Hz), 6.65 (1H, s), 6.97 (1H, s), 7.0–7.6 (42H, m), 8.20 (1H, d, J=6.9 Hz), 8.84 (2H, d, J=6.9 Hz), 9.52 (1H, d, J=8.4 Hz)

EXAMPLE 17

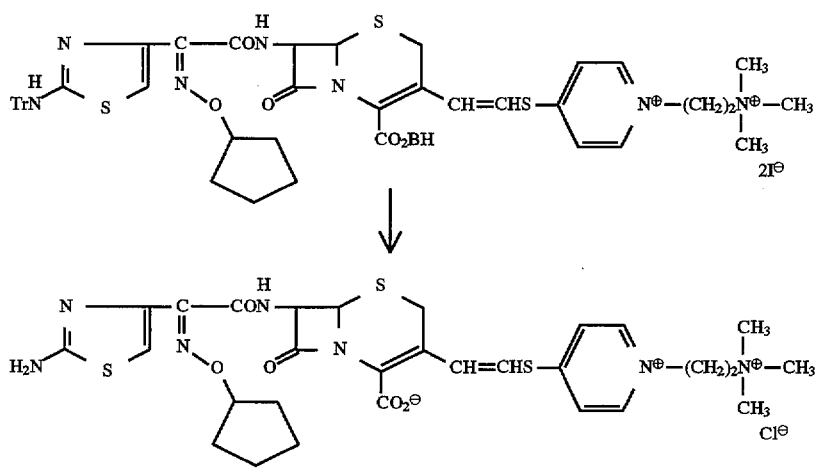

A 3.1 ml quantity of 88% formic acid and 0.268 ml of concentrated hydrochloric acid were added to a solution of 1.41 g of benzhydryl 7-[2-cyclopentyloxyimino-2-(2-tritylaminothiazol-4-yl)acetamido]-3-[2-(1-(2-trimethylammonioethyl)-4-pyridinio)thiovinyl]-3-cephem-4-carboxylate iodide in 4.7 ml of chloroform. The mixture was stirred at room temperature for 3 hours. After completion of the reaction, the formic acid layer was washed with chloroform (5 ml, three times). The mixture was added dropwise to diisopopyl ether/acetone (7.6 ml/28 ml) to form a precipitate, which was collected by filtration, giving 0.57 g of a crude product of 7-[2-cyclopentyloxyimino-2-(2-aminothiazol-4-yl)acetamido]-3-[2-(1-(2-trimethylammonioethyl)-4-pyridinio)thiovinyl]-3-cephem-4-carboxylate. The crude product was dissolved in water, and the solution was adsorbed on a column using a hyperporous polymer (Mitsubishi Kasei Corp., Diaion HP-21). Elution was carried out with water and with water/acetonitrile. The fractions containing the desired compound were collected, concentrated under reduced pressure and lyophilized to give 0.42 g of chloride 7-[2-cyclopentyloxyimino-2-(2-aminothiazol-4-yl)acetoamide]-3-[2-(1-(2-trimethylammonioethyl)-4-pyridinio)thiovinyl]-3-cephem-4-carboxylate.

$^1$H-NMR(DMSO-$d_6$) δppm; 1.4–1.9 (8H, m), 3.19 (9H, s), 3.57 (1H, d, J=17.0 Hz), 3.83 (1H, d, J=17.0 Hz), 4.0–4.1 (2H, m), 4.62 (1H, m), 5.0–5.1 (2H, m), 5.11 (1H, d, J=5.1 Hz), 5.66 (1H, dd, J=5.1 Hz, 8.4 Hz), 6.61 (1H, d, J=15.3 Hz), 6.68 (1H, s), 7.22 (2H, brs), 7.41 (1H, d, J=15.3 Hz), 8.09 (2H, d, J=6.9 Hz), 8.95 (2H, d, J=6.9 Hz), 9.48 (1H, d, J=8.4 Hz)

EXAMPLE 18

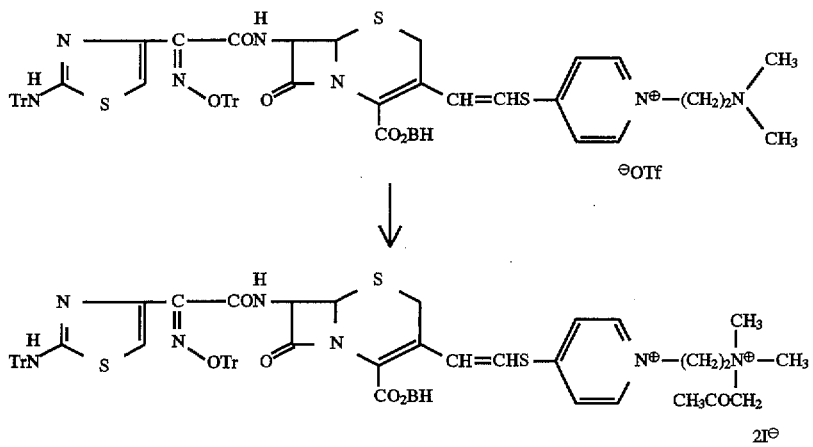

The procedure of Example 4 was followed to produce 3.51 g of benzhydryl 7-[2-trityloxyimino-2-(2-tritylaminothiazol-4-yl)acetamido]-3-[2-(1-(2-acetoniledimethylammonioethyl)-4-pyridinio)thiovinyl]-3-cephem-4-carboxylate iodide from 3.0 g of benzhydryl 7-[2-trityloxyimino-2-(2-tritylaminothiazol-4-yl)acetamido]-3-[2-(1-(2-dimethylaminoethyl)-4-pyridinio)thiovinyl]-3-cephem-4-carboxylate trifluoromethane sulfonate and 885 µm of iode acetone.

$^1$H-NMR(DMSO-$d_6$) δppm; 2.15 (3H, s), 3.25 (6H, s), 3.77 (1H, ABq, J=17.0 Hz), 4.0–4.1 (2H, m), 4.18 (1H, ABq, J=17.0 Hz), 4.64 (2H, brs), 4.9–5.0 (2H, m), 5.34 (1H, d, J=5.3 Hz), 5.98 (1H, dd, J=5.3 Hz, 8.3 Hz), 6.62 (1H, s), 6.99 (1H, s), 7.0–7.6 (42H, m), 8.20 (2H, d, J=6.9 Hz), 8.83 (2H, d, J=6.9 Hz), 9.95 (1H, d, J=8.3 Hz)

EXAMPLE 19

The procedure of Example 4 was followed to produce 2.61 g of benzhydryl 7-[2-trityloxyimino-2-(2-tritylaminothiazol-4-yl)acetamido]-3-[2-(1-(2-benzhydryloxycarbonylmethyl-dimethylammonioethyl)-4-pyridinio)thiovinyl]-3-cephem-4-carboxylate bromide from 2.5 g of benzhydryl 7-[2-trityloxyimino-2-(2-tritylaminothiazol-4-yl)acetamido]-3-[2-(1-(2-dimethylaminoethyl)-4-pyridinio)thiovinyl]-3-cephem-4- carboxylate trifluoromethane sulfonate and 8.32 g of benzhydryl 2-bromoacetate.

$^1$H-NMR(DMSO-$d_6$) δppm; 3.31 (6H, s), 3.77 (1H, ABq, J=17.0 Hz), 4.05–4.15 (2H, m), 4.18 (1H, ABq, J=17.0 Hz), 4.84 (2H, brs), 5.0–5.1 (2H, m), 5.34 (1H, d, J=5.1Hz), 5.98 (1H, dd, J=5.1 Hz, 8.3 Hz), 6.62 (1H, s), 6.90 (1H, s), 6.99 (1H, s), 7.0–7.6 (52H, m), 8.20 (2H, d, J=6.6 Hz), 8.90 (2H, d, J=6.6 Hz), 9.95 (1H, d, J=8.3 Hz)

EXAMPLE 20

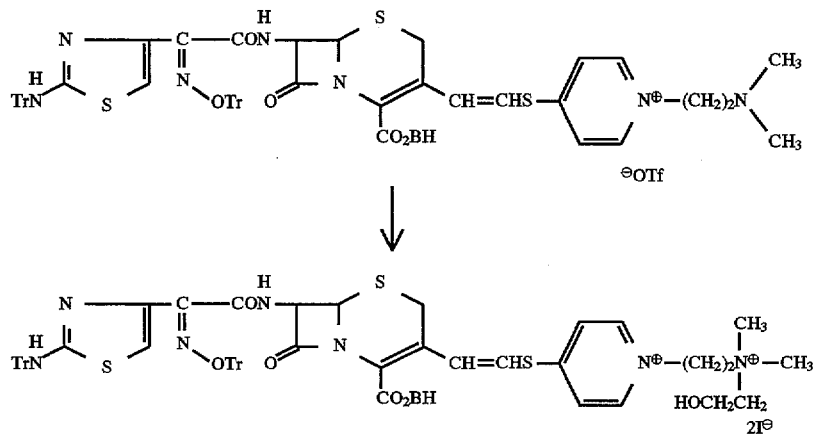

The procedure of Example 4 was followed to produce 3.21 g of benzhydryl 7-[2-trityloxyimino-2-(2-tritylaminothiazol-4-yl)acetamido]-3-[2-(1-(2-hydroxyethyl-dimethylammonioethyl)-4-pyridinio) thiovinyl]-3-cephem-4-carboxylate iodide from 3.0 g of benzhydryl 7-[2-trityloxyimino-2-(2-tritylaminothiazol-4-yl)acetamido]-3-[2-(1-(2-dimethylaminoethyl)-4-pyridinio) thiovinyl]-3-cephem-4-carboxylate trifluoromethane sulfonate and 19 g of 2-iodoethanol.

$^1$H-NMR(DMSO-$d_6$) δppm; 3.18 (6H, s), 3.5–3.6 (2H, m), 3.74 (1H, ABq, J=17.0 Hz), 3.8–3.9 (2H, m), 3.9–4.0 (2H, m), 4.18 (1H, ABq, J=17.0 Hz), 4.9–5.0 (2H, m), 5.37 (1H, d, J=5.1 Hz), 5.98 (1H, dd, J=5.1 Hz, 8.3 Hz), 6.62 (1H, s), 6.99 (1H, s), 7.0–7.6 (42H, m), 8.19 (2H, d, J=6.9 Hz), 8.82 (2H, d, J=6.9 Hz), 9.95 (1H, d, J=8.3 Hz)

EXAMPLE 21

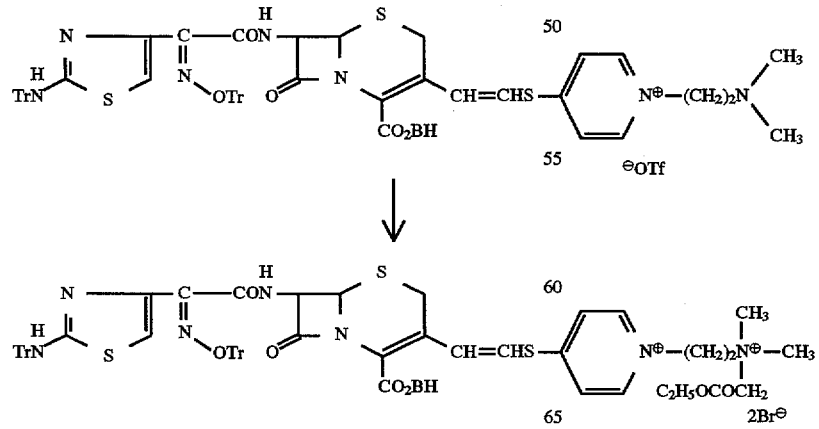

The procedure of Example 4 was followed to produce 2.5 g of benzhydryl 7-[2-trityloxyimino-2-(2-tritylaminothiazol-4-yl)acetamido]-3-[2-ethyloxycarbonylmethyl-dimethylammonioethyl)-4-pyridinio)thiovinyl]-3-cephem-4-carboxylate bromide from 2.5 g of benzhydryl 7-[2-trityloxyimino-2-(2-tritylaminothiazol-4-yl)acetamido]-3-[2-(1-(2-dimethylaminoethyl)-4-pyridinio)thiovinyl]-3-cephem-4-carboxylate trifluoromethane sulfonate and 3.0 ml of ethyl 2-bromoacetate.

$^1$H-NMR(DMSO-$d_6$) δppm; 1.22 (3H, t, J=7.2 Hz), 3.30 (6H, s), 3.77 (1H, ABq, J=17.0 Hz), 4.05–4.15 (2H, m), 4.18 (1H, ABq, J=17.0 Hz), 4.19 (2H, q, J=7.2 Hz), 4.56 (2H, brs), 5.0–5.1 (2H, m), 5.37 (1H, d, J=4.8 Hz), 5.98 (1H, dd, J=4.8 Hz, 8.1 Hz), 6.62 (1H, s), 6.98 (1H,s), 7.0–7.6 (42H, m), 8.20 (2H, d, J=7.0 Hz), 8.90 (2H, d, J=7.0 Hz), 9.95 (1H, d, J=8.1 Hz)

EXAMPLE 22

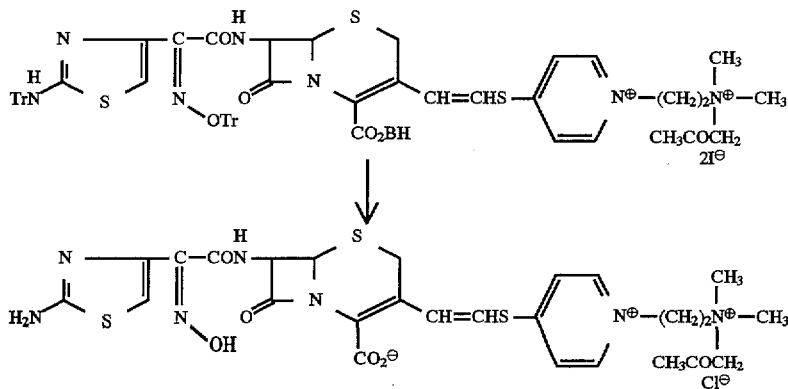

The procedure of Example 3 was followed to produce 535 mg of chloride 7-[2-hydroxyimino-2-(2-aminothiazol-4-yl)acetamido]-3-[2-(1-(2-acetoniledimethylammonioethyl)-4-pyridinio)thiovinyl]-3-cephem-4-carboxylate from 3.5 g of benzhydryl 7-[2-trityloxyimino-2(2-tritylaminothiazol-4-yl)acetamido]-3-[2-(1-(2-acetonyl-dimethylammonioethyl)-4-pyridinio)thiovinyl]-3-cephem-4-carboxylate iodide.

$^1$H-NMR(DMSO-$d_6$) δppm; 2.15 (3H, s), 3.28 (6H, s), 3.56 (1H, ABq, J=17.0 Hz), 3.79 (1H, ABq, J=17.0 Hz), 4.1–4.2 (2H, m), 4.84 (2H, brs), 5.0–5.1 (2H, m), 5.13 (1H, d, J=5.3 Hz), 5.69 (1H, dd, J=5.3 Hz, 8.3 Hz), 6.53 (1H, d, J=15.3 Hz), 6.62 (1H, s), 7.13 (2H, brs), 7.41 (1H, d, J=15.3 Hz), 8.05 (2H, d, J=6.9 Hz), 8.91 (2H, d, J=6.9 Hz), 9.43 (1H, d, J=8.3 Hz), 11.5 (1H, s)

EXAMPLE 23

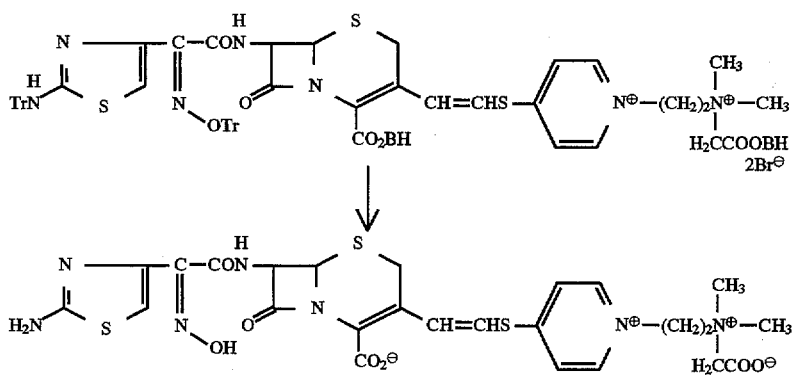

The procedure of Example 3 was followed to produce 289 mg of 7-[2-hydroxyimino-2-(2-aminothiazol-4-yl)acetamido]-3-[2-(1-(2-carboxylate methyldimethylammonioethyl)-4-pyridinio)thiovinyl]-3-cephem-4-carboxylate from 2.41 9 of benzhydryl 7-[2-trityloxyimino-2-(2-tritylaminothiazol-4-yl)acetamido]-3-[2-(1-(2-benzhydryloxycarbonylmethyl-dimethylammonioethyl)-4-pyridinio)thiovinyl]-3-cephem-4-carboxylate bromide.

$^1$H-NMR(DMSO-$d_6$) δppm; 3.18 (6H, s), 3.54 (1H, ABq, J=17.0 Hz), 3.71 (2H, brs), 3.75 (1H, ABq, J=17.0 Hz), 4.08–4.18 (2H, m), 4.8–4.9 (2H, m), 5.06 (1H, d, J=5.1 Hz), 5.65 (1H, d, J=5.1 Hz), 6.54 (1H, d, J=15.3 Hz), 6.64 (1H, s), 7.39 (1H, d, J=15.3 Hz), 7.94 (2H, d, J=6.9 Hz), 8.68 (2H, d, J=6.9 Hz)

EXAMPLE 24

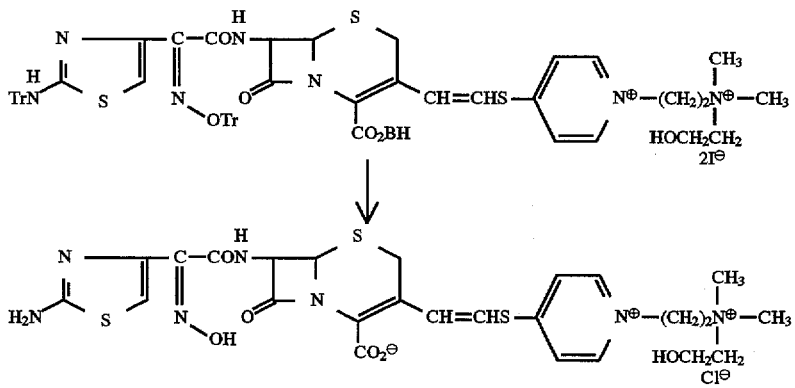

The procedure of Example 3 was followed to produce 160 mg of chlordie 7-[2-hydroxyimino-2-(2-aminothiazol-4-yl)acetamido]-3-[2-(1-(2-hydroxyethyldimethylammonioethyl)-4-pyridinio)thiovinyl]-3-cephem-4-carboxylate from 3.2 g of benzhydryl 7-[2-trityloxyimino-2-(2-tritylaminothiazol-4-yl)acetamido]-3-[2-(1-(2-hydroxyethyl-dimethylammonioethyl)-4-pyridinio)thiovinyl]-3-cephem-4-carboxylate iodide.

$^1$H-NMR(DMSO-$d_6$) δppm; 3.21 (6H, s), 3.55 (2H, brs), 3.64 (1H, ABq, J=17.0 Hz), 3.85 (2H, brs), 4.08 (1H, ABq, J=17.0 Hz), 4.0–4.1 (2H, m), 5.0–5.1 (2H, m), 5.19 (1H, d, J=5.1 Hz), 5.80 (1H, dd, J=5.1Hz, 8.3 Hz), 6.65 (1H, s), 7.02 (1H, d, J=15.3 Hz), 7.13 (2H, brs), 7.34 (1H, d, J=15.3 Hz), 8.18 (2H, d, J=6.9 Hz), 9.00 (2H, d, J=6.9 Hz), 9.48 (1H, d, J=8.3 Hz), 11.35 (1H, s)

EXAMPLE 25

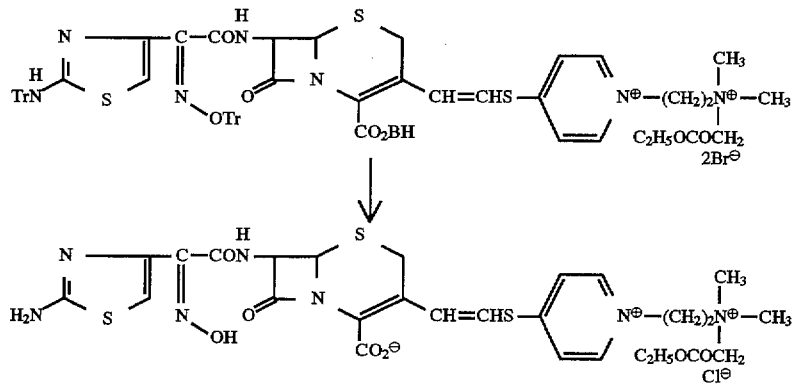

The procedure of Example 3 was followed to produce 320 mg of chloride 7-[2-hydroxyimino-2-(2-aminothiazol-4-yl) acetamido]-3-[2-(1-(2-ethyloxycarbonylmethyl-dimethylammonioethyl)-4-pyridinio)thiovinyl]-3-cephem-4-carboxylate from 2.49 g of benzhydryl 7-[2-trityloxyimino-2-(2-tritylaminothiazol-4-yl) acetamido]-3-[2-(1-(2-ethyloxycarbonylmethyl-dimethylammonioethyl)-4-pyridinio)thiovinyl]-3-cephem-4-carboxylate bromide.

$^1$H-NMR(DMSO-$d_6$) δppm; 1.23 (3H, t, J=7.2 Hz), 3.29 (6H, s), 3.67 (1H, ABq, J=17.0 Hz), 4.08 (1H, ABq, J=17.0 Hz), 4.18 (2H, q, J=7.2 Hz), 4.1–4.2 (2H, m), 4.60 (2H, brs), 5.0–5.1 (2H, m), 5.20 (1H, d, J=4.8 Hz), 5.80 (1H, dd, J=4.8 Hz, 8.1 Hz), 6.65 (1H, s), 7.02 (1H, d, J=15.0 Hz), 7.12 (2H, brs), 7.35 (1H, d, J=15.0 Hz), 8.19 (2H, d, J=7.0 Hz), 8.95 (2H, d, J=7.0 Hz), 9.48 (1H, d, J=8.1 Hz), 11.32 (1H, s)

EXAMPLE 26

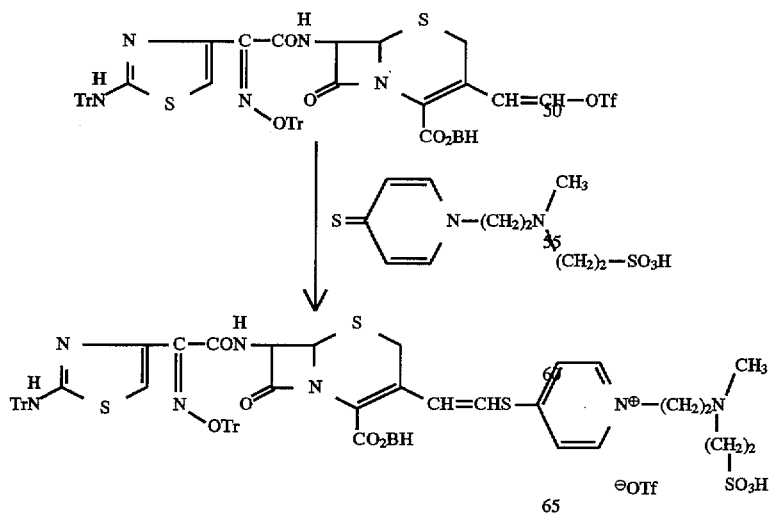

In anhydrous dimethylformamide (11 ml) were dissolved 2.5 g of benzhydryl 7-[2-trityloxyimino-2-(2-tritylaminothiazol-4-yl)acetamido]-3-(2-trifluoromethanesulfonyloxyvinyl)-3-cephem-4-carboxylate and 0.75 g of 1-(2-sulfoethyl-methylaminoethyl)-4-pyridothione. The solution was stirred at room temperature for 6 hours. After completion of the reaction, ethyl acetate was added to the reaction mixture after which the mixture was washed with an aqueous solution of sodium bicarbonate and with an aqueous solution of sodium chloride. The organic layer was dried over anhydrous magnesium sulfate. The organic solvent was distilled off under reduced pressure. The residue was dissolved in 15 ml of methylene chlordie. The solution was added dropwise to 150 ml of isopropyl ether to produce a precipitate. The precipitate was collected by filtration and dried under reduced pressure, giving 1.4 g of the contemplated benzhydryl 7-[2-trityloxyimino-2-(2-tritylaminothiazol-4-yl)acetoamido]-3-[2-(1-(2-sulfoethyl-methylaminoethyl)-4-pyridinio)thiovinyl]-3-cephem-4-carboxylate trifluoromethane sulfonate.

$^1$H-NMR(DMSO-$d_6$) δppm; 2.17 (3H, brs), 2.4–2.5 (2H, m), 2.7–2.8 (2H, m), 2.7–2.8 (2H, m), 3.76 (1H, ABq, J=17.7 Hz), 4.17 (1H, ABq, J=17.7 Hz), 4.5–4.6 (2H, m), 5.34 (1H, d, J=5.1Hz), 5.97 (1H, dd, J=5.1 Hz, 8.4 Hz), 6.62 (1H, s), 6.98 (1H, s), 7.1–7.5 (42H, m), 8.05 (2H, d, J=6.9 Hz), 8.76 (1H, s), 8.78 (2H, d, J=6.9 Hz), 9.94 (1H, d, J=8.4 Hz)

EXAMPLE 27

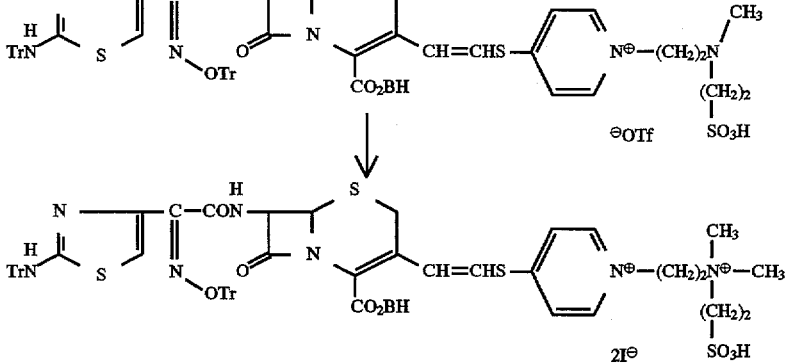

The procedure of Example 10 was followed to produce 0.63 g of the contemplated benzhydryl 7-[2-trityloxyimino-2-(2-tritylaminothiazol-4-yl)acetamido]-3-[2-(1-(2-sulfoethyl-dimethylammonioethyl)-4-pyridinio)thiovinyl]-3-cephem-4-carboxylate iodide from 0.67 g of benzhydryl 7-[2-trityloxyimino-2-(2-tritylaminothiazol-4-yl)acetoamido]-3-[2-(1-(2-sulfoethyl-dimethylaminoethyl)-4-pyridinio)thiovinyl]-3-cephem-4-carboxylate trifluoromethane sulfonate.

$^1$H-NMR(DMSO-d$_6$) δppm; 3.0–3.1 (2H, m), 3.13 (6H, s), 3.7–3.8 (2H, m), 3.83 (1H, ABq, J=17.4 Hz), 3.8–3.9 (2H, m), 4.18 (1H, ABq, J=17.4 Hz), 4.9–5.0 (2H, m), 5.35 (1H, d, J=5.1 Hz), 5.98 (1H, dd, J=5.1 Hz, 8.4 Hz), 6.62 (1H, s), 6.98 (1H, s), 7.1–7.5 (42H, m), 8.18 (2H, d, J=7.2 Hz), 8.79 (1H, s), 8.85 (2H, d, J=7.2 Hz), 9.94 (1H, d, J=8.4 Hz)

EXAMPLE 28

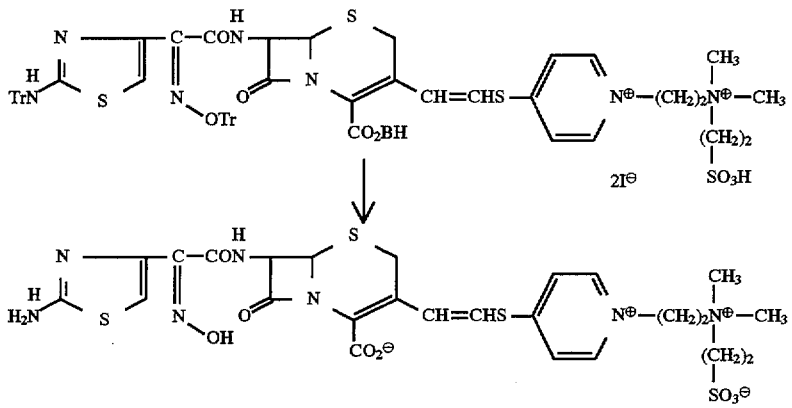

The procedure of Example 3 was followed to produce 0.15 g of 7-[2-hydroxyimino-2-(2-aminothiazol-4-yl)acetamido]-3-[2-(1-(2-sulfonate ethyldimethylammonioethyl)-4-pyridinio)thiovinyl]-3-cephem-4-carboxylate from 0.61 g of benzhydryl 7-[2-trityloxyimino-2-(2-tritylaminothiazol-4-yl)acetoamido]-3-[2-(1-(2-sulfoethyl-dimethylammonioethyl)-4-pyridinio)thiovinyl]-3-cephem-4-carboxylate iodide $^1$H-NMR(DMSO-d$_6$+D$_2$O) δppm; 3.0–3.1 (2H, m), 3.13 (6H, s), 3.54 (1H, ABq, J=17.1 Hz), 3.6–3.7 (2H, m), 3.76 (1H, ABq, J=17.1 Hz), 3.8–3.9 (2H, m), 4.85–4.95 (2H, m), 5.07 (1H, d, J=4.8 Hz), 5.66 (1H, d, J=4.8 Hz), 6.55 (1H, d, J=15.3 Hz), 7.42 (1H, d, J=15.3 Hz), 8.01 (2H, d, J=7.1 Hz), 8.73 (2H, d, J=7.1 Hz)

What we claim is:

1. A cephem compound represented by the formula

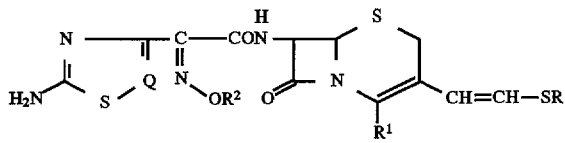

wherein Q represents CH or N, R$^1$ represents a carboxylate or a carboxyl group, R$^2$ represents a hydrogen atom, an optionally substituted lower alkyl group, an optionally substituted lower alkenyl group, an optionally substituted lower alkynyl group, an optionally substituted lower cycloalkyl group, an optionally substituted carboxy(lower)alkyl group, an optionally substituted hydroxy(lower)alkyl group, or an optionally substituted lower alkoxy(lower)alkyl group, and R represents

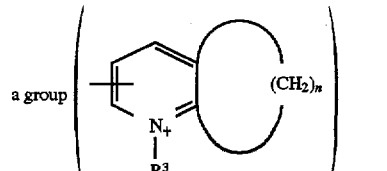

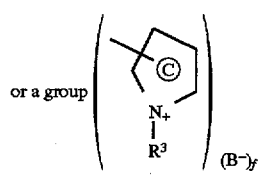

wherein R$^3$ represents a group —(CH$_2$)$_m$—Y or a group —(CH$_2$)$_m$—CO—Y (wherein m is an integer of 1 to 5, and Y represents a quaternary ammonium group), n is an integer of 0 to 4, B$^-$ represents an anion, f is 0 or 1 when R$^1$ represents a carboxylate, and 2 when R$^1$ represents a carboxyl group, and the ring C represents a 5-membered heterocyclic group of not more than 4 nitrogen atoms, which may be substituted by a lower alkyl group, a cephemcarboxy-protecting ester thereof and a nontoxic salt thereof.

2. The compound according to claim 1 wherein Q is CH.

3. The compound according to claim 2 wherein R represents

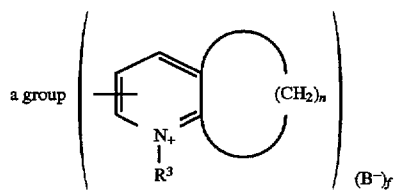

wherein R$^3$ represents a group —(CH$_2$)$_m$—Y, and n, B$^-$, f, m and Y are as defined hereinbefore.

4. The compound according to claim 2 wherein $R^2$ represents a hydrogen atom or a lower cycloalkyl group.

5. The compound according to claim 4 wherein R represents a group 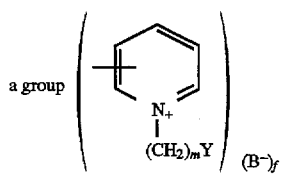

wherein $B^-$, f, m and Y are as defined hereinbefore.

6. At least one cephem compound selected from the group consisting of:

chloride 7-[2-hydroxyimino-2-(2-aminothiazol-4-yl)acetamido]-3-[2-(1-(3-(4-methylmorpholinio)propyl)-4-pyridinio)thiovinyl]-3-cephem-4-carboxylate or its salt, chloride 7-[2-hydroxyimino-2-(2-aminothiazol-4-yl)acetamido]-3-[2-(1-(2-trimethylammonioethyl)-4-pyridinio)thiovinyl]-3-cephem-4-carboxylate or its salt, chloride 7-[2-hydroxyimino-2-(2-aminothiazol-4-yl)acetamido]-3-[2-(1-(2-carbamoylmethyl-dimethylammonioethyl)-4-pyridinio)thiovinyl]-3-cephem-4-carboxylate or its salt, chloride 7-[2-hydroxyimino-2-(2-aminothiazol-4-yl)acetamido]-3-[2-(1-(2-(4-methylmorpholinio)ethyl)-4-pyridinio)thiovinyl]-3-cephem-4-carboxylate or its salt, chloride 7-[2-hydroxyimino-2-(2-aminothiazol-4-yl)acetamido]-3-[2-(1-(2-acetonyl-dimethylammonioethyl)-4-pyridinio)thiovinyl]-3-cephem-4-carboxylate or its salt, chloride 7-[2-hydroxyimino-2-(2-aminothiazol-4-yl)acetamido]-3-[2-(1-(2-(1-methylpiperidinio)ethyl)-4-pyridinio)thiovinyl]-3-cephem-4-carboxylate or its salt, 7-[2-hydroxyimino-2-(2-aminothiazol-4-yl)acetamido]-3-[2-(1-(2-carboxylate methyldimethylammonioethyl)-4-pyridinio)thiovinyl]-3-cephem-4-carboxylate or its salt, chloride 7-[2-hydroxyimino-2-(2-aminothiazol-4-yl)acetamido]-3-[2-[1-(2-hydroxyethyl-dimethylammonioethyl)-4-pyridinio)thiovinyl]-3-cephem-4-carboxylate or its salt, chloride 7-[2-hydroxyimino-2-(2-aminothiazol-4-yl)acetamido]-3-[2-(1-(2-ethyloxycarbonylmethyldimethylammonioethyl)-4-pyridinio])thiovinyl]-3-cephem-4-carboxylate or its salt, chloride 7-[2-cyclopentyloxyimino-2-(2-aminothiazol-4-yl)acetamide]-3-[2-(1-(2-trimethylammonioethyl)-4-pyridinio)thiovinyl]-3-cephem-4-carboxylate or its salt, and 7-[2-hydroxyimino-2-(2-aminothiazol-4-yl)-acetamido]-3-[2-(1-(sulfonate ethyl-dimethylammonioethyl)-4-pyridinio)thiovinyl]-3-cephem-4-carboxylate or its salt.

7. An antimicrobial composition comprising a cephem compound represented by the formula

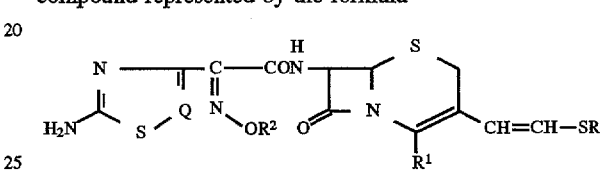

wherein Q, $R^1$, $R^2$ and R are as defined hereinbefore, a cephemcarboxy-protective ester thereof or a nontoxic salt thereof, and a pharmaceutically acceptable carrier.

8. The antimicrobial composition according to claim 7 which has a high antimicrobial activity against methicillin-resistant *Staphylococcus aureus*.

* * * * *